United States Patent
Paone et al.

(10) Patent No.: US 7,732,438 B2
(45) Date of Patent: Jun. 8, 2010

(54) CGRP RECEPTOR ANTAGONISTS

(75) Inventors: Daniel V. Paone, Lansdale, PA (US); Anthony W. Shaw, Harleysville, PA (US); Craig M. Potteiger, Reading, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 533 days.

(21) Appl. No.: 11/665,520

(22) PCT Filed: Oct. 12, 2005

(86) PCT No.: PCT/US2005/036659

§ 371 (c)(1),
(2), (4) Date: Apr. 12, 2007

(87) PCT Pub. No.: WO2006/044449

PCT Pub. Date: Apr. 27, 2006

(65) Prior Publication Data

US 2007/0287697 A1      Dec. 13, 2007

Related U.S. Application Data

(60) Provisional application No. 60/618,715, filed on Oct. 14, 2004.

(51) Int. Cl.
C07D 401/00   (2006.01)
C07D 487/00   (2006.01)
A61K 31/55    (2006.01)
A61P 25/00    (2006.01)

(52) U.S. Cl. .......................... 514/214.02; 514/217.05; 540/579; 540/599

(58) Field of Classification Search .......... 540/579, 540/599; 514/214.02, 217.05
See application file for complete search history.

(56) References Cited

FOREIGN PATENT DOCUMENTS

WO   WO 2004/092166   10/2004

OTHER PUBLICATIONS

Supplementary Search Report for counterpart EPO Appln. No. 05803913.2.

*Primary Examiner*—Bruck Kifle
(74) *Attorney, Agent, or Firm*—Gerard Devlin; Raynard Yuro

(57) ABSTRACT

Compounds of Formula (I) and Formula (II) (where variables $R^1$, $R^2$, $R^4$, A, B, W, X, Y and Z are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

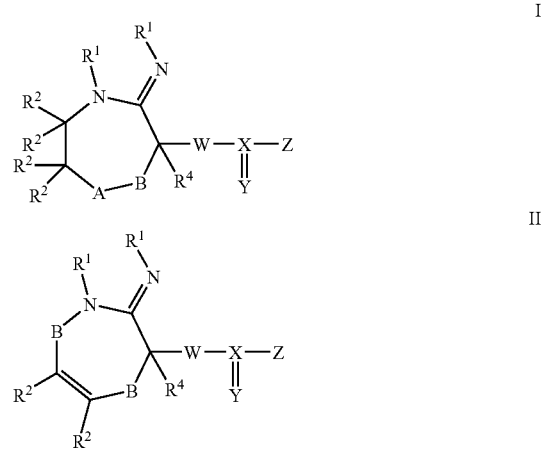

6 Claims, No Drawings

CGRP RECEPTOR ANTAGONISTS

RELATED APPLICATION DATA

This is a National filing under 35 USC 371 of PCT/US2005/036659, filed Oct. 12, 2005, which claims priority from U.S. Ser. No. 60/618,715, filed Oct. 14, 2004.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human $\alpha$-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP (8-37), a peptide CGRP antagonist (Williamson et al., Cephalalgia, 1997, 17, 525-531). Trigeminal ganglion stimulation increased facial blood flow in the rat, which was inhibited by CGRP (8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache. Compelling evidence of the efficacy of CGRP antagonists for the treatment of migraine has been provided by clinical studies using intravenously administered BIBN4096BS. This CGRP antagonist was found to be a safe and effective acute treatment for migraine (Olesen et al., N. Engl. J. Med., 2004, 350(11), 1104-1110).

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

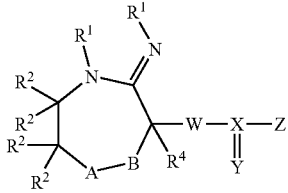

I and formula II:

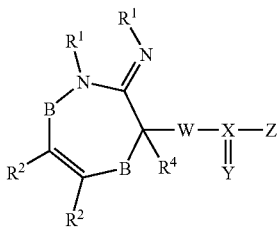

II (where variables $R^1$, $R^2$, $R^4$, A, B, W, X, Y and Z are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

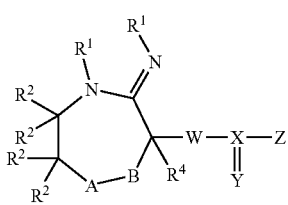

I wherein:

Z is selected from:

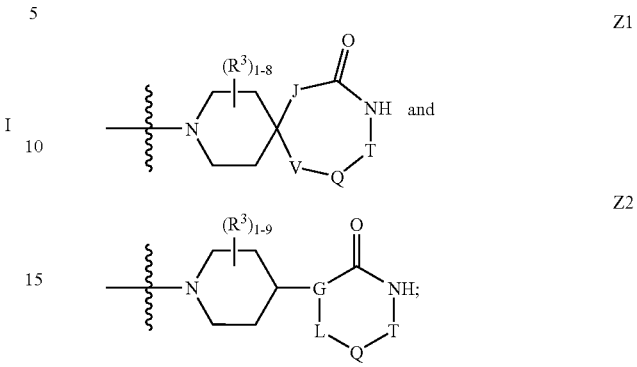

A is a bond, $C(R^2)_2$, O, $S(O)_m$ or $NR^2$;

B is $(C(R^2)_2)_n$;

$R^1$ is independently selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and,
   v) $O(CO)R^4$;
2) aryl or heteroaryl, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$, j) $CO_2R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;
where any two independent $R^1$ and the atom or atoms to which they are attached optionally join to form a ring selected from $C_{5-7}$ heterocycle, including dihydro-imidazolyl, tetrahydro-pyrimidyl, and tetrahydro-diazepinyl;

$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and,
   v) $O(CO)R^4$;
2) aryl or heteroaryl, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   P) $SO_2NR^{10}R^{11}$,
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and
   v) $O(CO)R^4$,
   where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_pC_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl, or morpholinyl, which is ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

X is C or S;

Y is O, $(R^4)_2$, NCN, $NSO_2CH_3$ or $NCONH_2$, or Y is $O_2$ when X is S;

$R^6$ is independently selected from H and:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   $N(R^{10})(CO)OR^{11}$,
   P) $SO_2NR^{10}R^{11}$
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and
   v) $O(CO)R^4$;

J is a bond, $C(R^6)_2$, O or $NR^6$;

V is selected from a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=$N,N(R^6)$—$C(R^6)_2$, $N$=$C(R^6)$, and $N(R^6)$—$N(R^6)$;

G-L is selected from: N, N—$C(R^6)_2$, C=$C(R^6)$, C=N, $C(R^6)$, $C(R^6)$—$C(R^6)_2$, $C(R^6)$—$C(R^6)_2$—$C(R^6)_2$, C=C$(R^6)$—$C(R^6)_2$, $C(R^6)$—$C(R^6)$=$C(R^6)$, $C(R^6)$—$C(R^6)_2$—N$(R^6)$, C=$C(R^6)$—$N(R^6)$, $C(R^6)$—$C(R^6)$=N, $C(R^6)$—N$(R^6)$—$C(R^6)_2$, C=N—$C(R^6)_2$, $C(R^6)$—N=$C(R^6)$, $C(R^6)$—$N(R^6)$—$N(R^6)$, C=N—$N(R^6)$, N—$C(R^6)_2$—$C(R^6)_2$, N—C$(R^6)$=$C(R^6)$, N—$C(R^6)_2$—$N(R^6)$, N—$C(R^6)$=N, N—N$(R^6)$—$C(R^6)_2$ and N—N=$C(R^6)$;

Q is independently selected from:
(1) =$C(R^{7a})$—,
(2) —$C(R^{7a})_2$—,
(3) —$C(=O)$—,
(4) —$S(O)_m$—,
(5) =N—, and
(6) —$N(R^{7a})$—;

T is independently selected from:
(1) =$C(R^{7b})$—,
(2) —$C(R^{7b})_2$—,
(3) —$C(=O)$—,
(4) —$S(O)_m$,
(5) =N—, and
(6) —$N(R^{7b})$—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$ cycloalkyl, aryl, heterocycle, and heteroaryl, which ring is unsubstituted or substituted with 1-10 substituents each independently selected from $R^6$;

p is 0 to 2q+1, for a substituent with q carbons;

m is 0, 1 or 2;

n is 0 or 1;

s is 1, 2 or 3;

and pharmaceutically acceptable salts and individual diastereomers thereof

Further embodiments of the invention are CGRP antagonists of Formula I which include compounds of the Formula Ia:

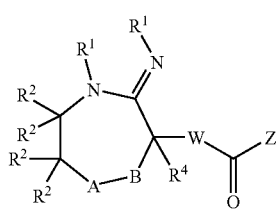

Ia wherein:

A is a bond, $C(R^2)_2$, O, $S(O)_m$ or $NR^2$;

B is $(C(R^2)_2)_n$;

n is 0 or 1; and $R^1$, $R^2$, $R^4$, W, Z, and m are as defined in Formula I;

and pharmaceutically acceptable salts and individual stereoisomers thereof.

Additional embodiments of the invention are CGRP antagonists of Formula I which include compounds of the Formula Ib:

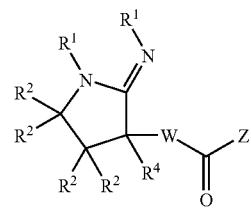

Ib wherein:

$R^1$, $R^2$, $R^4$, W, Z, and m are as defined in Formula I;

and pharmaceutically acceptable salts and individual stereoisomers thereof.

Additional embodiments of the invention are CGRP antagonists of Formula I which also include compounds of the Formula Ic:

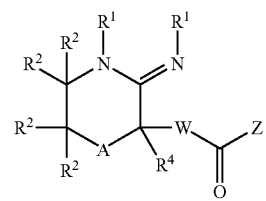

Ic wherein:

A is $C(R^2)_2$, O, $S(O)_m$ or $NR^2$;

$R^1$, $R^2$, $R^4$, W, Z, and m are as defined in Formula I;

and pharmaceutically acceptable salts and individual stereoisomers thereof.

Additional embodiments of the invention are CGRP antagonists of Formula I which include compounds of the Formula Id:

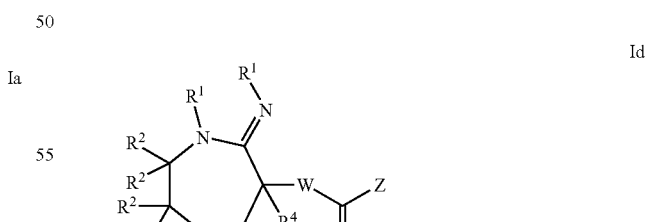

Id wherein:

A is $C(R^2)_2$, O, $S(O)_m$ or $NR^2$;

$R^1$, $R^2$, $R^4$, W, Z, and m are defined in Formula I;

and pharmaceutically acceptable salts and individual stereoisomers thereof.

Further embodiments of the invention are CGRP antagonists of Formulae Ia-Id, wherein:

$R^1$ is selected from:
1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10} R^{11}$, and
   m) $O(CO)R^4$; and
2) aryl or heteroaryl, unsubstituted or substituted with one or more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and,
   m) $O(CO)R^4$;
   where any two independent $R^1$ and the atom or atoms to which they are attached optionally join to form a ring selected from $C_{5-7}$ heterocycle, including dihydroimidazolyl, tetrahydro-pyrimidyl, and tetrahydro-diazepinyl;

$R^2$ is selected from:
1) H, $C_0$-$C_6$ alkyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and
2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$,
   where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

$R^6$ is independently selected from H and:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$ and
   m) $O(CO)R^4$; and J is a bond, $C(R^5)_2$, O, or $NR^5$, and V is a bond, $C(R^6)_2$, O, $S(O)_m$, $NR^6$, $C(R^6)_2$—$C(R^6)_2$, $C(R^6)$=$C(R^6)$, $C(R^6)_2$—N($R^6$), $C(R^6)$=N, $N(R^6)$—$C(R^6)_2$, N=$C(R^6)$ or $N(R^6)$—N($R^6$), such that when:

J is a bond, V is a bond and Z is Z1 the following structure forms:

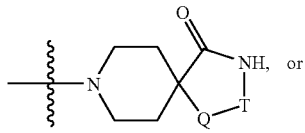

J is a bond, V is a bond, Z is Z1 and T is —C(=O)—, the following structure forms:

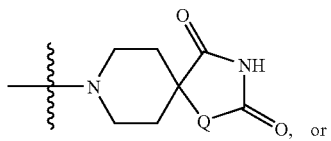

J is a bond and Z is Z1 the following structure forms:

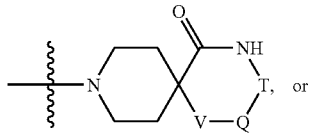

V is a bond and Z is Z1 the following structure forms:

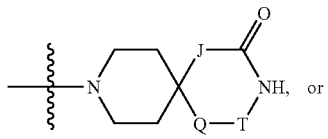

G-L is N, and Z is Z2 the following structure forms:

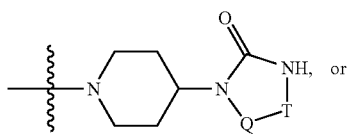

G-L is N—C($R^6$)$_2$, and Z is Z2 the following structure forms:

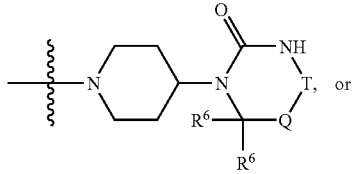

G-L is C=C($R^6$), and Z is Z2 the following structure forms:

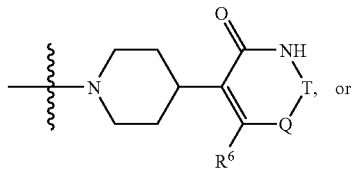

G-L is C=N, and Z is Z2 the following structure forms:

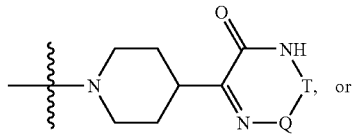

G-L is N—C($R^6$)$_2$—C($R^6$)$_2$, and Z is Z2 the following structure forms:

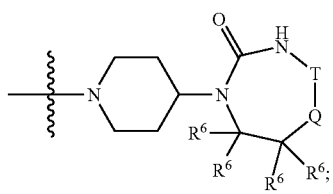

Q is independently selected from:
(1) =C($R^{7a}$)—,
(2) —C($R^{7a}$)$_2$—,
(3) —C(=O)—,
(4) —S(O)$_m$—,
(5) =N—, and
(6) —N($R^{7a}$)—;

T is independently selected from:
(1) =C($R^{7b}$)—,
(2) —C($R^{7b}$)$_2$—,
(3) —C(=O)—,
(4) —S(O)$_m$—,
(5) =N—, and
(6) —N($R^{7b}$)—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl, which ring is unsubstituted or substituted with 1-10 substituents each independently selected from $R^6$;

p is 0 to 2q+1, for a substituent with q carbons m is 0 to 2;

s is 1 to 3;

and pharmaceutically acceptable salts and individual stereoisomers thereof.

Still further embodiments of the invention are CGRP antagonists of Formulae Ia-Ie, wherein:

$R^1$ is selected from:
1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$,
   and where heteroaryl is selected from:
      imidazole, isoxazole, oxazole, pyrazine, pyrazole, pyridazine, pyridine, pyrimidine, and thiazole;
   e) heterocycle, unsubstituted or substituted with 1-5 substituents each independently selected from $R^4$, and where heterocycle is selected from: azetidine, dioxane, dioxolane, morpholine, oxetane, piperazine, piperidine, pyrrolidine, tetrahydrofuran, and tetrahydropyran;
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$,
   m) $O(CO)R^4$;
2) aryl or heteroaryl, selected from: phenyl, imidazole, isoxazole, oxazole, pyrazine, pyrazole, pyridazine, pyridine, pyrimidine, and thiazole,
   unsubstituted or substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$;

$R^2$ is selected from:
1) H, $C_0$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$,
      and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
   e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
   f) $(F)_p C_{1-3}$ alkyl,
   g) halogen,
   h) $OR^4$,
   i) $O(CH_2)_s OR^4$,
   j) $CO_2 R^4$.
   k) CN,
   l) $NR^{10}R^{11}$, and
   m) $O(CO)R^4$; and
2) aryl or heteroaryl, selected from:
   phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$,
   where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, $R^{10}$ and $R^{11}$ are independently selected from: H, $C_{1-6}$ alkyl, $(F)_p C_{3-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and phenyl, unsubstituted or substituted with hydroxy or $C_1$-$C_6$ alkoxy;

W is $NR^4$ or $C(R^4)_2$;

$R^6$ is independently selected from H and:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$, j) S(O)$_m$R$^4$,
k) CN,
l) NR$^{10}$R$^{11}$, and
m) O(CO)R$^4$;

J is a bond, V is a bond, Z is Z1, Q is —N(R$^{7a}$)—, and T is —C(=O)—, such that the following structure forms:

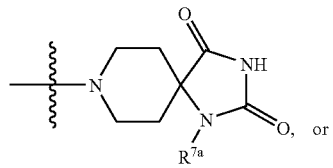

J is a bond, V is a bond, Z is Z1, Q is —C(R$^{7a}$)$_2$—, and T is —C(=O)—, such that the following structure forms:

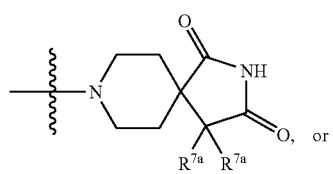

J is a bond, V is a bond, Z is Z1, Q is —N═, and T is ═C(R$^{7b}$)—, such that the following structure forms:

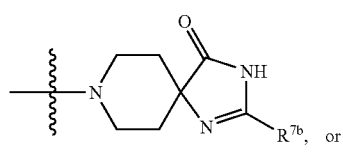

J is a bond, V is a bond, Z is Z1, Q is —C(R$^{7a}$)$_2$—, and T is —C(R$^{7b}$)$_2$—, such that the following structure forms:

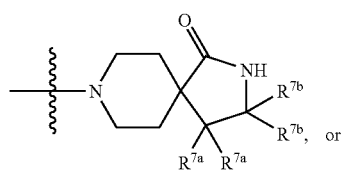

J is a bond, V is a bond, Z is Z1, Q is —C(R$^{7a}$)═, T is ═C(R$^{7b}$)—, and the atoms to which R$^{7a}$ and R$^{7b}$ are attached are joined together to form a benzene, pyridine, or diazine ring such that one of the following structures form:

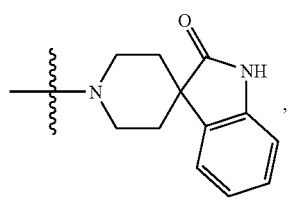

-continued

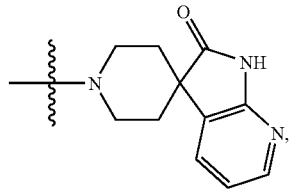

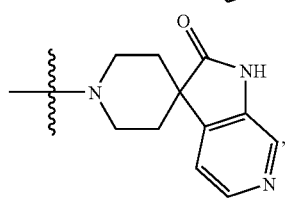

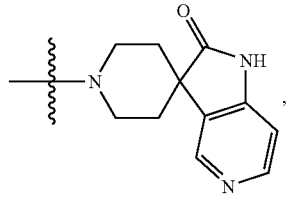

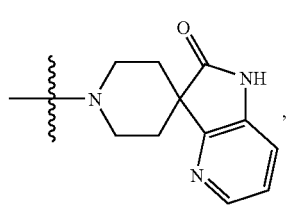

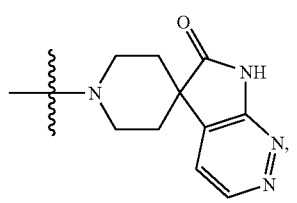

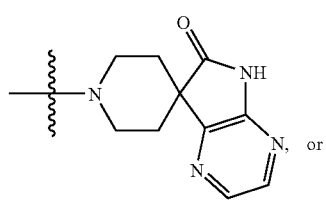

J is a bond, V is C(R$^6$)$_2$, Z is Z1, Q is —C(R$^{7a}$)═, T is ═C(R$^{7b}$)—, and the atoms to which R$^{7a}$ and R$^{7b}$ are attached are joined together to form a benzene, or pyridine ring such that one the following structures form:

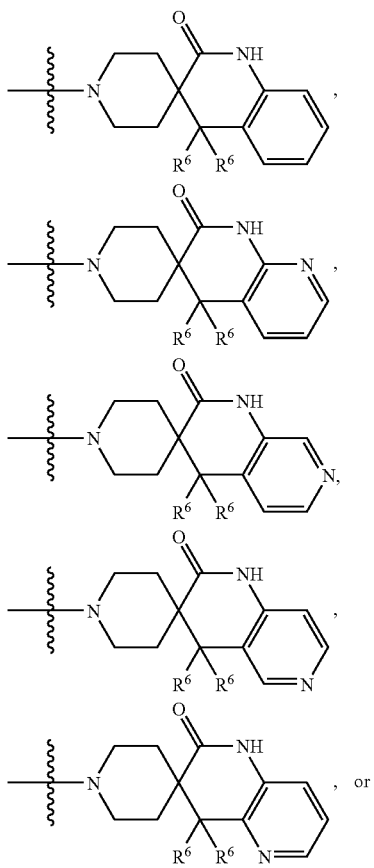

J is O, V is a bond, Z is Z1, Q is —C(R$^{7a}$)=, T is =C(R$^{7b}$)—, and the atoms to which R$^{7a}$ and R$^{7b}$ are attached are joined together to form a benzene, or pyridine ring such that one of the following structures form:

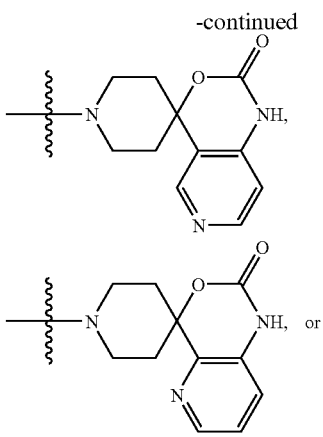

G-L is N, Z is Z2, Q is —C(R$^{7a}$)$_2$—, and T is —C(R$^{7b}$)$_2$—, such that the following structure forms:

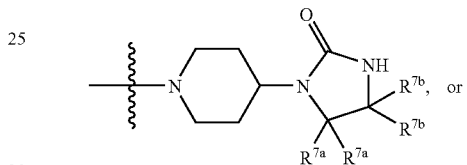

G-L is N, Z is Z2, Q is —C(R$^{7a}$)= and T is =C(R$^{7b}$)— such that the following structure forms:

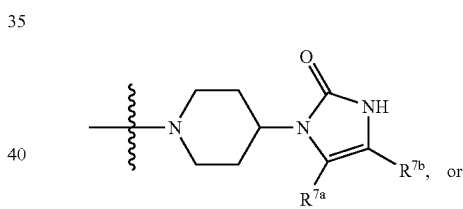

G-L is N, Z is Z2, Q is —N=, and T is =C(R$^{7b}$)—, such that the following structure forms:

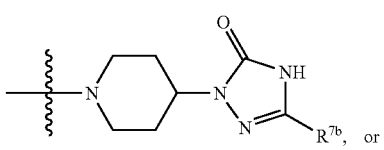

G-L is N, Z is Z2, Q is —C(R$^{7a}$)$_2$—, and T is —C(O)—, such that the following structure forms:

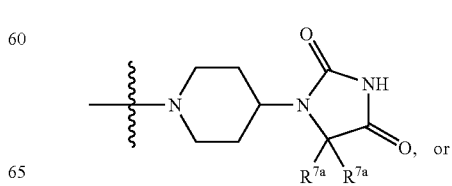

G-L is C=C(R⁶), Z is Z2, Q is —C(R⁷ᵃ)= and T is =C(R⁷ᵇ)—, such that the following structure forms:

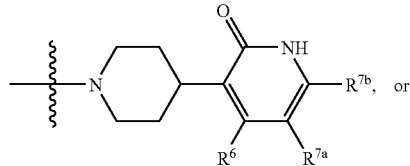

G-L is C=C(R⁶), Z is Z2, Q is —C(R⁷ᵃ)= and T is =N—, such that the following structure forms:

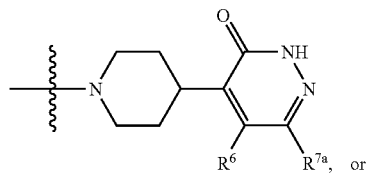

G-L is C=C(R⁶), Z is Z2, Q is —N— and T is =C(R⁷ᵇ)—, such that the following structure forms:

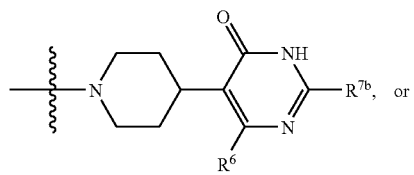

G-L is C=N, Z is Z2, Q is —C(R⁷ᵃ)= and T is =C(R⁷ᵇ)—, such that the following structure forms:

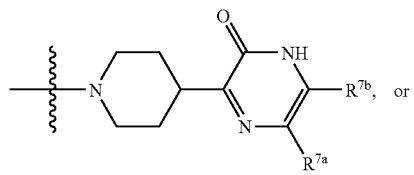

G-L is N, Z is Z2, Q is —C(R⁷ᵃ)=, and T is =C(R⁷ᵇ)—, and the atoms to which R⁷ᵃ and R⁷ᵇ are attached are joined together to form a benzene, pyridine, or diazine ring such that one of the following structures form:

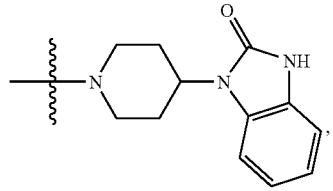

-continued

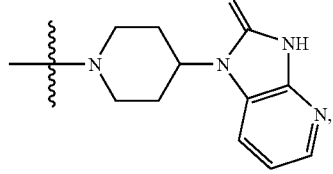

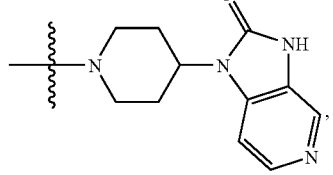

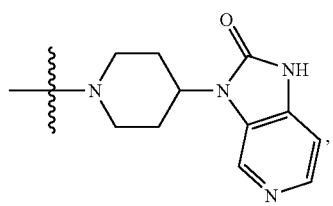

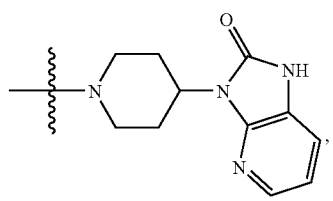

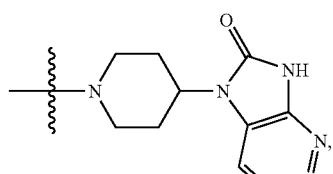

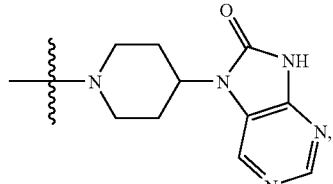

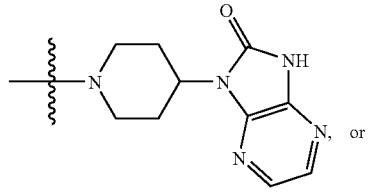

G-L is N—C(R⁶)₂, Z is Z2, Q is —C(R⁷ᵃ)=, and T is =C(R⁷ᵇ)—, and the atoms to which R⁷ᵃ and R⁷ᵇ are attached are joined together to form a benzene, or pyridine ring such that one of the following structures form:

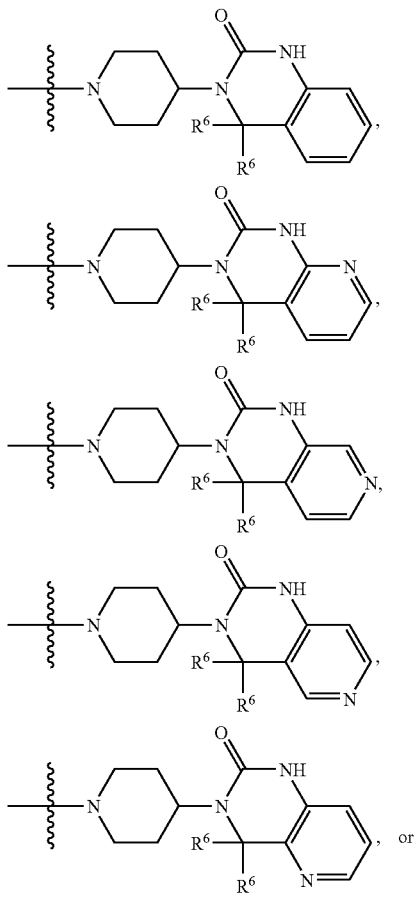

G-J is C=N, Z is Z2, Q is —C($R^{7a}$)=, and T is =C($R^{7b}$)—, and the atoms to which $R^{7a}$ and $R^{7b}$ are attached are joined together to form a benzene ring such that the following structure forms:

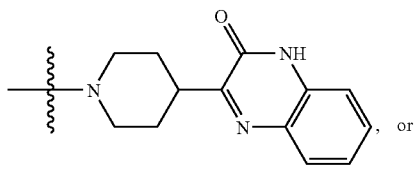

G-L is C=C($R^6$), Z is Z2, Q is —C($R^{7a}$)=, and T is =C($R^{7b}$)—, and the atoms to which $R^{7a}$ and $R^{7b}$ are attached are joined together to form a benzene ring such that the following structure forms:

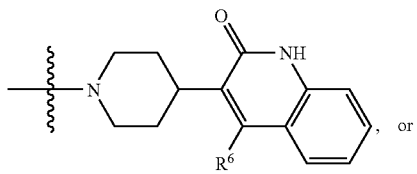

G-L is N—C($R^6$)$_2$—C($R^6$)$_2$, Z is Z2, Q is —C($R^{7a}$)=, and T is =C($R^{7b}$)—, and the atoms to which $R^{7a}$ and $R^{7b}$ are attached are joined together to form a benzene ring such that the following structure forms:

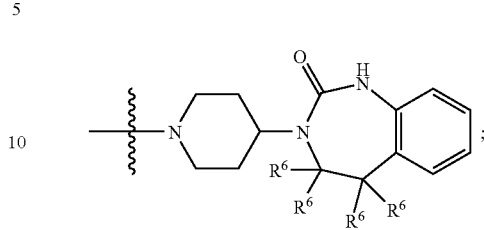

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$ cycloalkyl, aryl, heterocycle, and heteroaryl which is unsubstituted or substituted with 1-10 substituents each independently selected from $R^6$;

p is 0 to 2q+1, for a substituent with q carbons m is 0 to 2;

s is 1 to 3;

and pharmaceutically acceptable salts and individual stereoisomers thereof

Another embodiment of the invention includes CGRP antagonists which include compounds of Formula II:

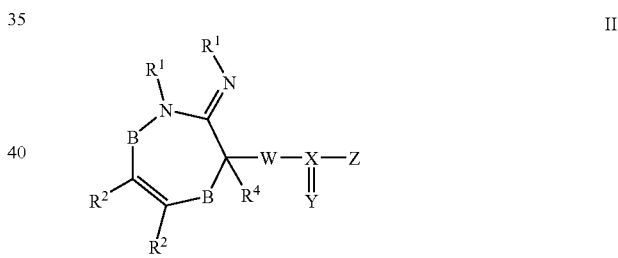

wherein:

B, J, Q, T, V, W, X, Y, $R^1$, $R^2$, R3 and R4 are as defined in Formula I, and pharmaceutically acceptable salts and individual diastereomers thereof.

It is to be understood that where one or more of the above recited structures or substructures recite multiple substituents having the same designation each such variable may be the same or different from each similarly designated variable. For example, $R^2$ is recited four times in Formula I, and each $R^2$ in Formula I may independently be any of the substructures defined under $R^2$. The invention is not limited to structures and substructures wherein each $R^2$ must be the same for a given structure. The same is true with respect to any variable appearing multiple time in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not every substituent or combination of substituents which are said to form rings are capable of forming a ring structure in every circumstance or situation. Moreover, even those substituents capable of ring formation may or may not form a ring structure in every circumstance or situation.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_p C_{1-3}$ alkyl" this means that when there is one carbon, there are 2(1)+1=3 fluorines. When there are two carbons, there are 2(2)+1=5 fluorines, and when there are three carbons there are 2(3)=1=7 fluorines.

When variables G and L are presented or depicted as "G-L" this indicates that G and L together represent a particular moiety. G-L may represent a single ring atom or various arrangements of multiple ring atoms. For instance, G-L is at times herein defined as the single ring atom N, and is at other times defined as multiple ring atoms N—$C(R^6)_2$, C=$C(R^6)$, and so forth.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 ml of binding buffer [10 mM HEPES, pH 7.4, 5 mM $MgCl_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 µg/ml streptomycin at 37° C., 95% humidity, and 5% $CO_2$. For cAMP assays, cells were plated at $5 \times 10^5$ cells/well in 96-well poly-D-lysine-coated plates (Becton-Dickinson) and cultured for ~18 h before assay. Cells were washed with phosphate-buffered saline (PBS, Sigma) then pre-incubated with 300 µM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3'PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/ml streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm² flasks. CRLR and RAMP1 expression constructs were co-transfected in equal amounts. Twenty-four hours after transfection the cells were diluted and selective medium (growth medium+300 µg/ml hygromycin and 1 µg/ml puromycin) was added the following day. A clonal cell line was generated by single cell deposition utilizing a FACS Vantage SE (Becton Dickinson). Growth medium was adjusted to 150 µg/ml hygromycin and 0.5 µg/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 µg of membranes were incubated in 1 ml binding buffer (10 mM HEPES, pH 7.4, 5 mM $MgCl_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% \ I_{max}/100)}{1 + ([Drug]/K_i(1 + [Radiolabel]/K_d)^{nH})} + (Y_{max} - Y_{min})(\% \ I_{max} - \% \ I_{min}/100)$$

Where Y is observed CPM bound, $Y_{max}$ is total bound counts, Y min is non specific bound counts, (Y max−Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a 5-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-βergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes. The synthesis of intermediates and final compounds may be conducted as described in Schemes 1-8.

Reaction Schemes

The preparation of final compounds proceeds through intermediates such as those of formula III and formula IV, and the synthesis of each intermediate is described herein.

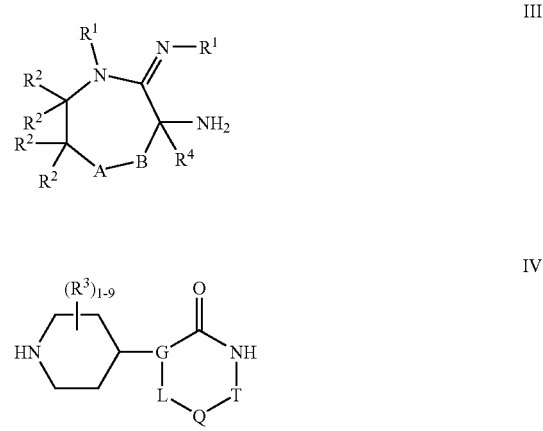

In general, intermediates of the formulas III and IV can be coupled through a urea linkage as shown in Scheme 1. The resulting amine after deprotection of intermediate I can be coupled with carbamoyl chloride intermediate 3 to produce urea 4. Other activated intermediates known to those skilled in the art can also be used to prepare compounds like 4.

SCHEME 1

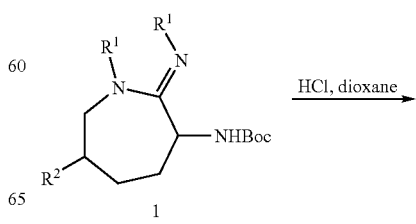

The synthesis of compounds represented by Intermediate IV can be accomplished by procedures similar to those described in Henning et al., *J. Med. Chem.*, 1987, 30, 814-819; Carpino et al., WO 96/35713; Brown et al., *J. Chem. Soc.* 1957, 682-686; Barlin et al., *Aust. J. Chem.* 1982, 35 (11), 2299-2306; and references cited therein.

Additionally, the synthesis of compounds represented by Intermediate IV can be accomplished according to Scheme 2. For example, a diamino heterocycle, such as 2,3-diaminopyridine 5, can be reductively alkylated with ketones such as 6 to give the monalkylated product 7 (Scheme 2). Ring closure with carbonyldiimidazole furnishes imidazolone 8. Final deprotection under standard conditions gives the intermediate 9.

Caprolactams can be assembled following an olefin metathesis strategy as outlined in Scheme 3. 2,4-Dimethoxybenzylamine hydrochloride is alkylated with 2,3-dibromopropene under mild basic conditions to give amine 11. (2R)-2-{[(benzyloxy)carbonyl]amino}pent-4-enoic acid (12), prepared in one step from commercially available D-allyl glycine according to known procedures (*J. Chem. Soc.*, 1962, 3963-3968), can be coupled to amine 11 under a variety of conditions to give amide 13. A variety of transition metal catalyzed cross couplings can be performed on the vinyl bromide, for example palladium-mediated arylations with phenylboronic acid and sodium carbonate, yielding styrene derivative 14. Ring-closing metathesis occurs in the presence of the Grubbs second generation ruthenium catalyst in dichloromethane with mild heating to afford lactam 15. Removal of the dimethoxybenzyl group and hydrogenation with in situ protection of the primary amine gives the corresponding saturated lactam 17. Treatment with Lawesson's reagent yields thioamide compounds of the general formula 18.

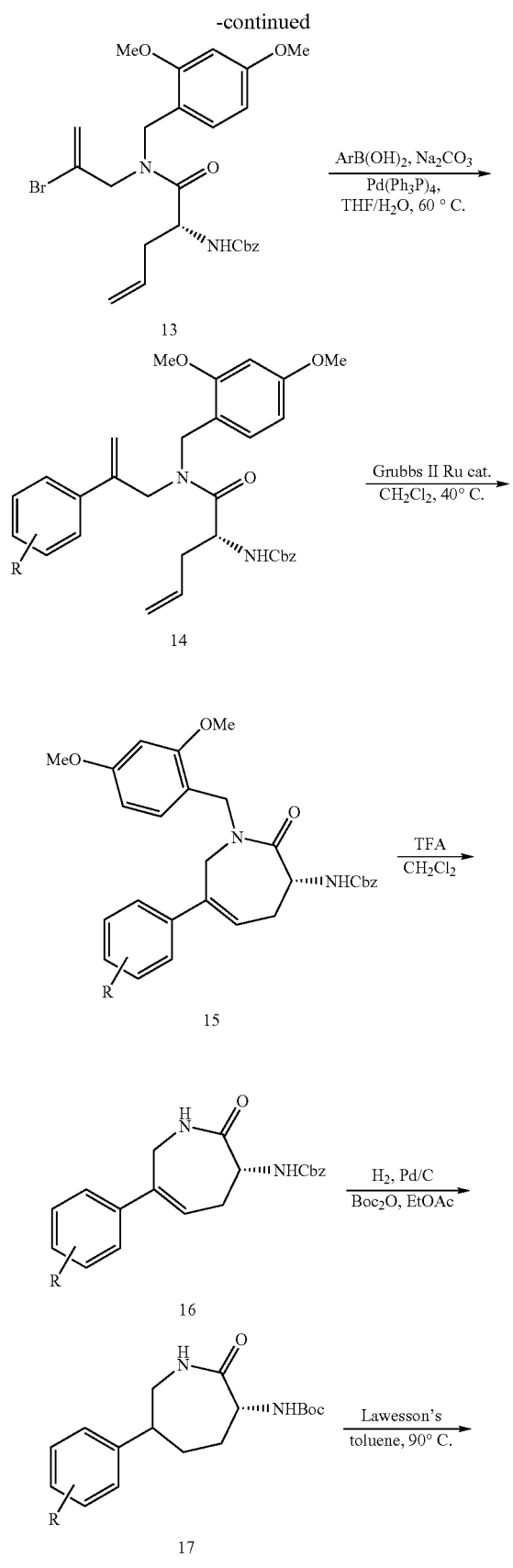

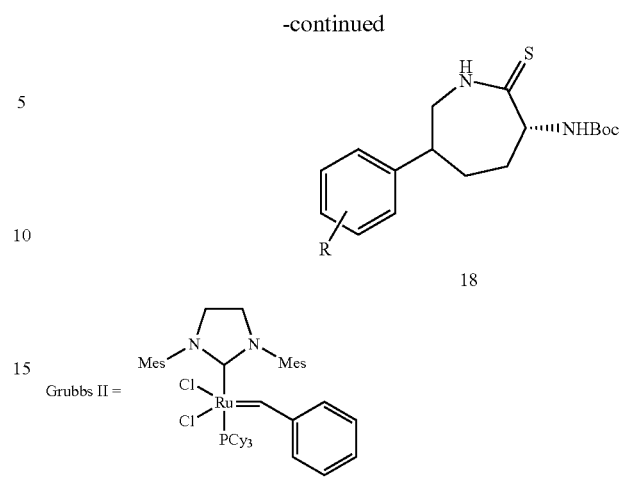

Alternatively, a C6-aryl group can be introduced as outlined in Scheme 4. Addition of nitromethane to the known glutamic acid derived aldehyde 19 (*Tetrahedron Asymmetry*, 1998, 3381-94), followed by in situ elimination affords nitro olefin 20. Addition of the aryl group via a boronic acid derivative, or similar equivalent, can be accomplished in a stereoselective manner through chiral ligand-Rh catalysis. Concomitant nitro reduction and benzyl ester hydrogenolysis affords the amino acid 22. Ring closure under standard conditions, followed by removal of a single tert-butoxycarbonyl group furnishes the lactam 24. Treatment with Lawesson's reagent yields thioamide compounds of the general formula 25.

SCHEME 4

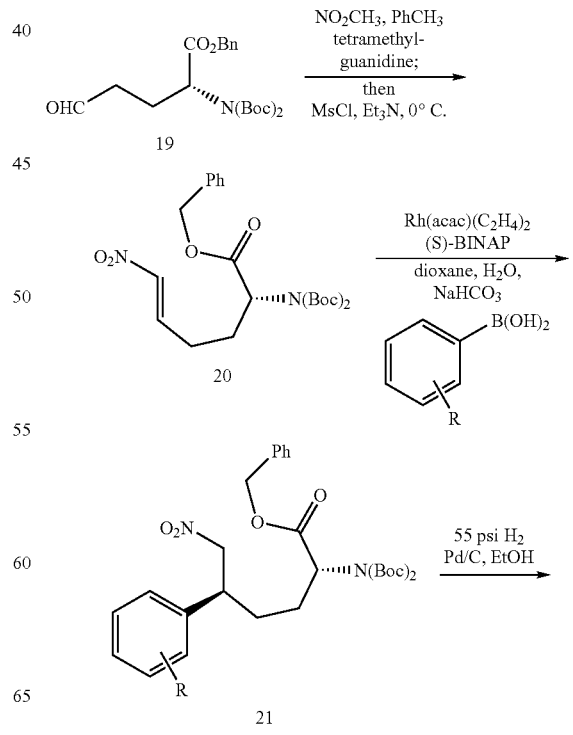

-continued

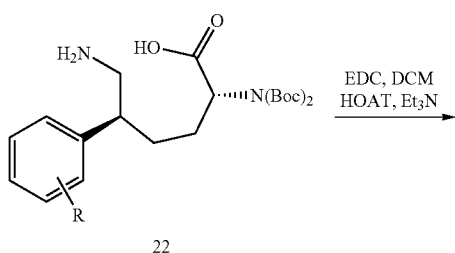

SCHEME 5

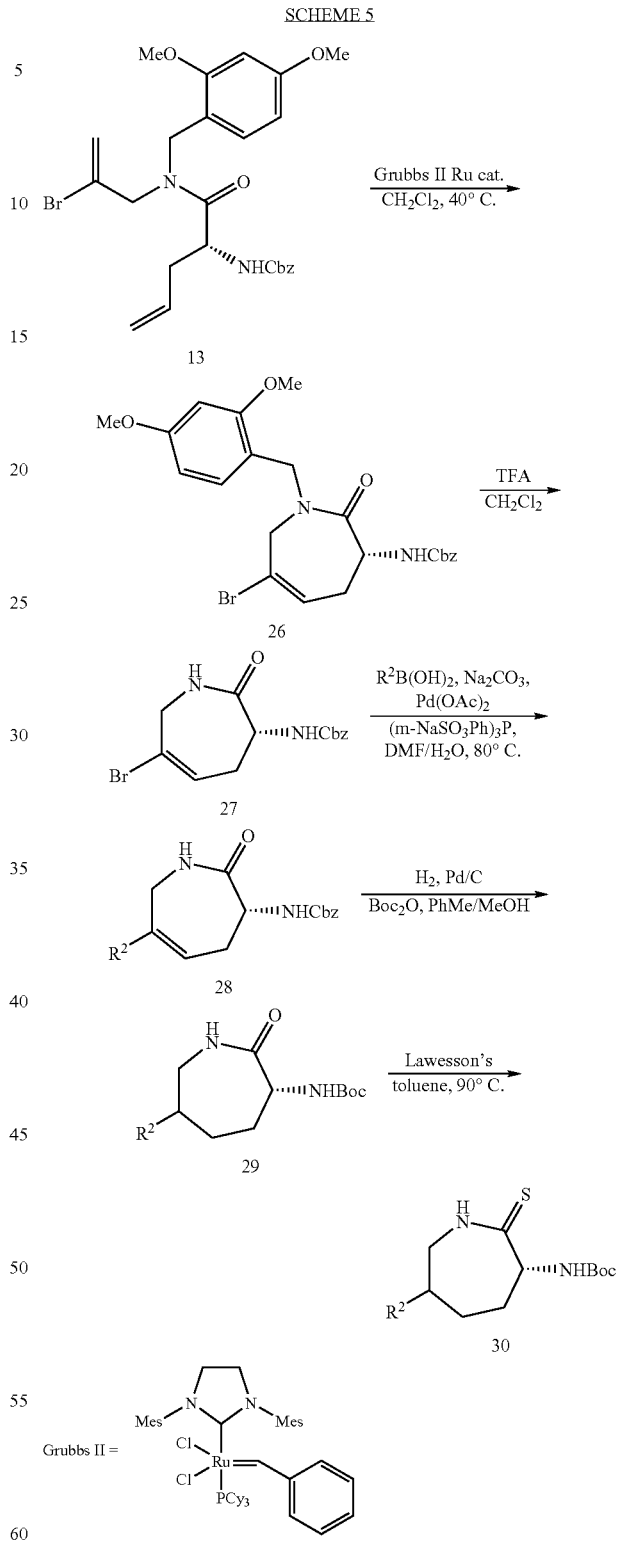

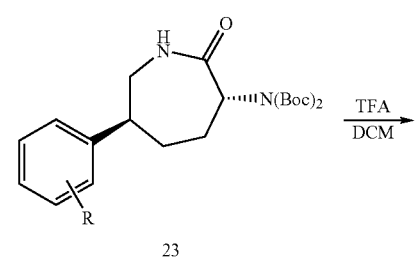

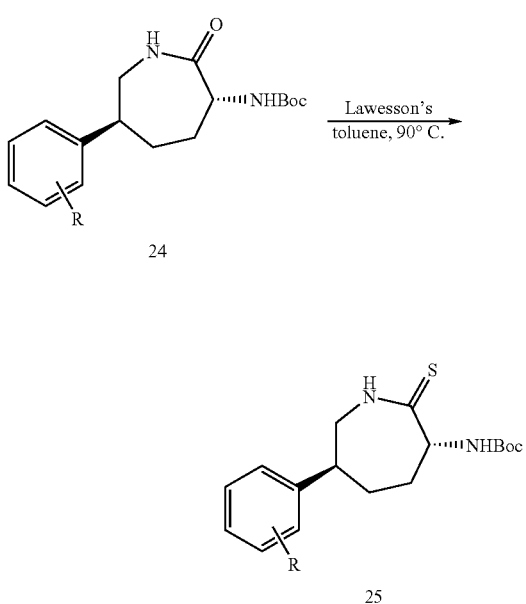

Variation at the 6-position of the caprolactams can be introduced by employing a similar strategy (Scheme 5). Ring-closing metathesis can be performed directly on vinyl bromide 13 using the Grubbs second generation ruthenium catalyst to give cyclic vinyl bromide 26. Removal of the dimethoxybenzyl group and palladium-mediated cross coupling, in this case with a boronic acid, furnishes compounds of the general formula 28. The transformation of 27 to 28 is not limited to boronic acid derivatives. After standard hydrogenation, treatment with Lawesson's reagent yields thioamide compounds of the general formula 30.

Alternatively, addition of a Grignard or similar reagent to the nitro olefin 31, followed by nitro reduction and benzyl ester hydrogenolysis affords various amino acids such as 33 (Scheme 6). Ring closure under standard conditions, followed by removal of a single tert-butoxycarbonyl group furnishes the lactam 29. Treatment with Lawesson's reagent yields thioamide compounds of the general formula 30.

SCHEME 6

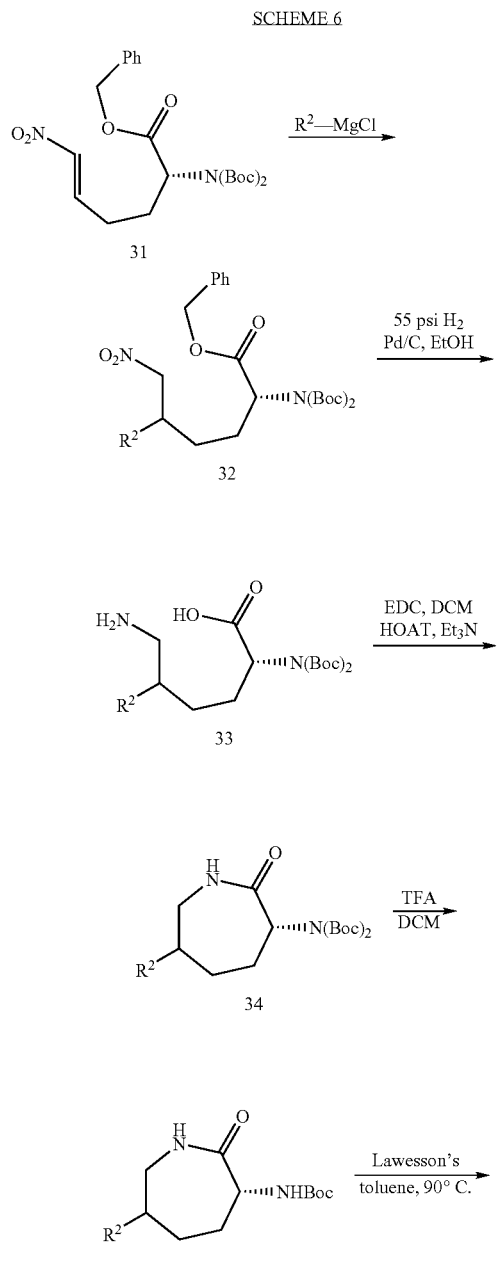

SCHEME 7

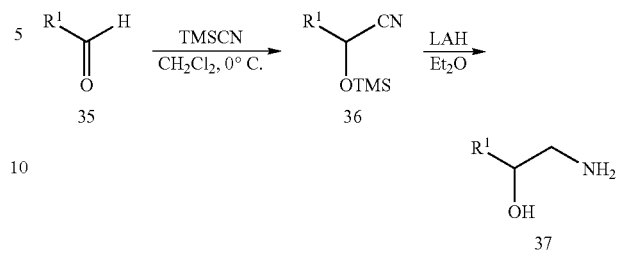

Cyclic amidines are prepared as shown in Scheme 8. Thioamide 30 is reacted with a variety of amino alcohols 37 in the presence of mercury(II) chloride to give amidines 38. Hydroxyl activation with methanesulfonyl chloride and ring closure gives cyclic amidines of the general formula I.

SCHEME 8

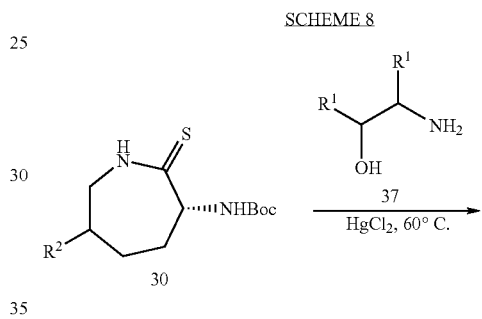

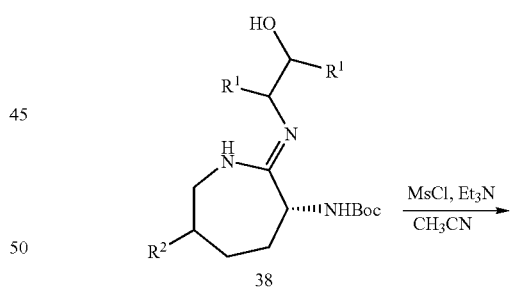

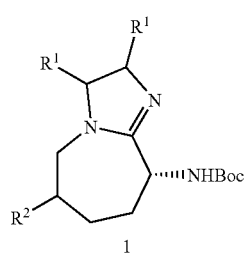

The required amino alcohols for imidazole synthesis were either commercially available or prepared as shown in Scheme 7. Treatment of aldehydes with trimethylsilyl cyanide gives cyanohydrins 36 which can be reduced to the appropriate amino alcohols 37 with lithium aluminum hydride.

INTERMEDIATES AND EXAMPLES

The following examples are provided so that the invention might be more fully understood. These examples are illustrative only and should not be construed as limiting the invention in any way.

Intermediate 1

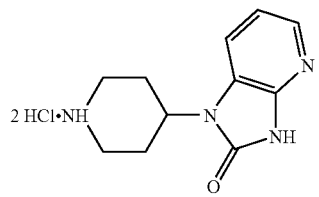

2-Oxo-1-(4-piperidinyl)-2,3-dihydro-1H-imidazo[4,5-b]pyridine dihydrochloride

Step A. 2-Amino-3-[(1-tert-butoxycarbonylpiperidin-4-yl)amino)pyridine

Sodium triacetoxyborohydride (14.5 g, 68.7 mmol) was added to a solution of 2,3-diaminopyridine (5.00 g, 45.8 mmol) and N-(tert-butoxycarbonyl)-4-piperidone (9.58 g, 48.1 mmol) in dichloroethane (75 mL) at room temperature. After 5 h, additional sodium triacetoxyborohydride was added (1.8 g) and again after another 2.5 h. The reaction was stirred overnight, and quenched with 5% aqueous sodium hydroxide. This was extracted with methylene chloride, and washed with 5% aqueous sodium hydroxide, water and saturated sodium chloride solution. After drying over sodium sulfate, the solution was filtered and evaporated to give the crude product. This was purified by chromatography (silica gel, 3 to 5% methanol in methylene chloride gradient elution), which gave the title compound (4.44 g). MS 293 (M+1) $^1$H NMR (500 MHz, CD$_3$OD) δ 7.32 (dd, J=5, 1 Hz, 1H), 6.85 (dd, J=8, 1 Hz, 1H), 6.59 (dd, J=8, 5 Hz, 1H), 4.04 (d, J=13 Hz, 2H), 3.46 (m, 1H), 2.98 (br s, 2H), 2.01 (dd, J=12, 2 Hz, 2H), 1.46 (s, 9H), 1.37 (qd, J=12, 4 Hz, 2H).

Step B. 2-Oxo-1-(1-tert-butoxycarbonylpiperidin-4-yl)-2,3-dihydro-1H-imidazo[4,5-b]pyridine Carbonyldiimidazole (0.70 g, 4.33 mmol) was added to a solution of 2-amino-3-[(1-tert-butoxycarbonylpiperidin-4-yl)amino]pyridine (1.15 g, 3.93 mmol) in acetonitrile (150 mL) at room temperature. After several hours, an additional amount of carbonyldiimidazole was added (0.81 g), and the reaction stirred overnight. The acetonitrile was evaporated in vacuo, the residue partitioned between water and chloroform, and the organic phase washed with saturated brine and dried over magnesium sulfate. The crude product was purified by chromatography (silica gel, 1.2 to 2.5% methanol in methylene chloride gradient elution), which gave the title compound (1.09 g). $^1$H NMR (500 MHz, CDCl$_3$) δ 9.39 (br s, 1H), 8.04 (dd, J=5, 1 Hz, 1H), 7.33 (dd, J=8, 1 Hz, 1H), 6.99 (dd, J=8, 5 Hz, 1H), 4.50 (m, 1H), 4.32 (br s, 2H), 2.86 (br s, 2H), 2.20 (m, 2H), 1.86 (d, J=12 Hz, 2H), 1.50 (s, 9H).

Step C. 2-Oxo-1-(4-piperidinyl)-2,3-dihydro-1H-imidazo[4,5-b]pyridine dihydrochloride 2-Oxo-1-(1-tert-butoxycarbonylpiperidin-4-yl)-2,3-dihydro-1H-imidazo[4,5-b]pyridine (1.03 g, 3.23 mmol) was dissolved in methanol (25 mL) and a solution of 2 N hydrochloric acid in ether (8 mL) was added at room temperature. After 2 h, the volatiles were removed in vacuo, to give the title compound (0.92 g). MS 219 (M+1). $^1$H NMR (500 MHz, CD$_3$OD) δ 8.01 (dd, J=6, 1 Hz, 1H), 7.83 (d, J=8 Hz, 1H), 7.28 (dd, J=8, 6 Hz, 1H), 4.60 (m, 1H), 3.59 (d, J=12 Hz, 2H), 3.21 (t, J=12 Hz, 2H), 2.70 (dq, J=13, 4 Hz, 2H), 2.12 (d, J=13 Hz, 2H).

Intermediate 2

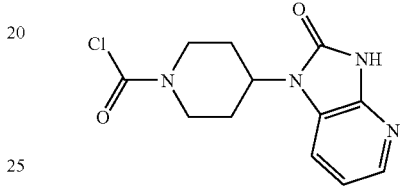

4-(2-Oxo-2,3-dihydro-1H-imidazo[4,5]pyridin-1-yl)piperidine-1-carbonyl chloride

Phosgene (20% wt. in toluene; 1.8 mL, 3.43 mmol) was added to a suspension of 2-oxo-1-piperidinium-4-yl-2,3-dihydro-1H-imidazo[4,5-b]pyridin-4-ium dichloride (100 mg, 0.343 mmol) and 2,6-lutidine (0.50 mL, 4.293 mmol) in dichloromethane (5 mL) at 0° C. After 2 h, the solution was added to saturated aqueous sodium bicarbonate and extracted with ethyl acetate. The organic layer was washed with water (2×), saturated brine, dried over magnesium sulfate, filtered and concentrated. Dichloromethane (10 mL) was added, and the mixture was filtered to give the title compound as a solid (48 mg). MS 281 (M+1). $^1$H NMR (500 MHz, (CD$_3$)$_2$SO) δ 11.58 (s, 1H), 7.90 (d, J=5.1 Hz, 1H), 7.67 (d, J=7.6 Hz, 1H), 7.01-6.99 (m, 1H), 4.52-4.46 (m, 1H), 4.31-4.23 (m, 2H), 3.38-3.33 (m, 1H), 3.19-3.14 (m, 1H), 2.32-2.24 (m, 2H), 1.84-1.81 (m, 2H).

Intermediate 3

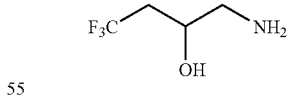

4,4,4-Trifluoro-2-hydroxybutan-1-aminium chloride 2-(2,2,2-Trifluoroethyl)oxirane (5.27 g, 41.8 mmol) was added to a solution of ammonia (2 M in methanol; 170 mL, 340 mmol) and the solution heated to 60° C. After 1.25 h, the mixture was allowed to cool to ambient temperature and concentrated to a volume of 20 mL. HCl (4 M in dioxane; 12 mL, 48 mmol) was added slowly and the mixture concentrated to give a white solid (4.0 g) that was 85% pure and contained 15% of a dimeric byproduct. MS 144.1 (M+H). $^1$H NMR (500 MHz, CD₃OD) δ 4.17-4.12 (m, 1H), 3.10 (dd, J=12.9, 2.9 Hz, 1H), 2.89 (dd, J=12.7, 9.8 Hz, 1H), 2.50, 2.35 (m, 2H).

Intermediate 4

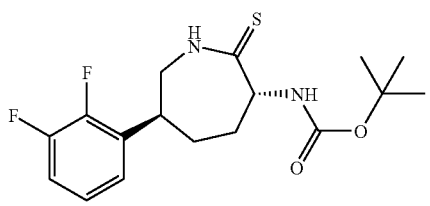

tert-Butyl (3R,6S)-6-(2,3-difluorophenyl)-2-thioxoazepan-3-ylcarbamate

Step A.
2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropene (10.9 g, 54.5 mmol) in dichloromethane (200 mL). After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B. Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C. Benzyl (1R)-1-{[[(2,3-difluorophebyl)prop-2-enyl](2,4-dimetho-benzyl-amino]carbonyl}but-3-enylcarbamate Dichloro[1,1'-bis(diphenylphosphino)ferrocene]palladium dichloromethane adduct (0.726 g, 0.889 mmol) was added to a solution of benzyl (1R)-1-{[(2-bromoprop-2-enyl)(2,4-dimethoxybenzyl)amino]carbonyl}but-3-enylcarbamate (9.2 g, 17.8 mmol), 2,3-difluorophenylboronic acid (2.95 g, 18.7 mmol) and sodium carbonate (2M in water; 19.6 mL, 39.1 mmol) in N,N-dimethylformamide (60 mL) and the mixture was heated to 75° C. After 2 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→55% ethyl acetate/hexanes) gave the title compound (6.8 g). MS 551.2 (M+1).

Step D. Benzyl (3R)-6-(2,3-difluorophenyl)-1-(2,4-dimethoxybenzyl)-2-oxo-2,3,4,7-tetrahydro-1H-azepin-3-ylcarbamate

[1,3-bis-(2,4,6-Trimethylphenyl-2-imidazolidinylidene) dichloro(phenylmethylene)-(tricyclohexylphosphine)ruthenium] (Grubbs second generation catalyst) (2.62 g, 3.09 mmol) was added to a solution of benzyl (1R)-1-{[[2-(2,3-difluorophenyl)prop-2-enyl](2,4-dimethoxybenzyl)amino] carbonyl}but-3-enylcarbamate (6.8 g, 12.35 mmol) in dichloromethane (1800 mL) and the solution was heated to 40° C. After 48 h, additional catalyst was added (0.52 g, 0.61 mmol) and the reaction continued to heat at 40° C. for an additional 48 h. The mixture was allowed to cool to ambient temperature and concentrated. Purification by silica gel chromatography (5% ethyl acetate/hexanes→55% ethyl acetate/hexanes) gave the title compound (3.71 g). MS 523.1 (M+1).

Step E. Benzyl (3R)-6-(2,3-difluorophenyl)-2-oxo-2,3,4,7-tetrahydro-1H-azepin-3-ylcarbamate Trifluoroacetic acid (60 mL) was added to a solution of benzyl (3R)-6-(2,3-difluorophenyl)-1-(2,4-dimethoxybenzyl)-2-oxo-2,3,4,7-tetrahydro-1H-azepin-3-ylcarbamate (3.70 g, 7.08 mmol) in dichloromethane (40 mL). After 18 h, the mixture was concentrated at 25° C., methanol (150 mL) was added, and the precipitate filtered. The filtrate was concentrated, diluted with dichloromethane (100 mL), washed with water (2×), saturated aqueous sodium bicarbonate (2×), saturated brine, dried over magnesium sulfate, filtered and concentrated. Purification by silica gel chromatography (5% ethyl acetate/hexanes→65% ethyl acetate/hexanes) gave the title compound (1.75 g). MS 373.1 (M+1).

Step F. tert-Butyl (3R,6S)-6-(2,3-difluorophenyl)-2-oxoazepan-3-ylcarbamate

10% Palladium on carbon (700 mg) was added to a solution of benzyl (3R)-6-(2,3-difluorophenyl)-2-oxo-2,3,4,7-tetrahydro-1H-azepin-3-ylcarbamate (2.6 g, 6.98 mmol) and di-tert-butyl dicarbonate (5.03 g, 23.0 mmol) in toluene (200 mL). The reaction vessel was evacuated and back-filled with nitrogen (3×), then back-filled with hydrogen (1 atm). After 24 h, the mixture was filtered and concentrated. Purification by preparative reverse phase chromatography (DeltaPak C18, 15µ, 47 mm×300 mm, 70 mL/min: 80% H₂O/NH₄OAc: 20% CH₃CN to 100% CH₃CN over 60 min) afforded the pure trans title compound (1.2 g). MS 341.2 (M+1). ¹H NMR (500 MHz, CDCl₃) δ 7.07-7.04 (m, 2H), 6.91-6.89 (m, 1H), 6.04 (br s, 1H), 5.93 (d, J=5.6 Hz, 1H), 4.46 (dd, J=10.5, 4.6 Hz, 1H), 3.65-3.59 (m, 1H), 3.21 (dd, J=15.1, 7.3 Hz, 1H), 3.05-3.00 (m, 1H), 2.25-2.20 (m, 1H), 2.17-2.10 (m, 2H), 1.79-1.71 (m, 1H), 1.46 (s, 9H).

Step G: tert-Butyl (3R,6S)-6-(2,3-difluorophenyl)-2-thioxoazepan-3-ylcarbamate

Lawesson's reagent [2,4-Bis(4-methoxyphenyl)-1,3-dithia-2,4-diphosphetane-2,4-disulfide] (2.90 g, 7.18 mmol) was added to a suspension of tert-butyl (3R,6S)-6-(2,3-difluorophenyl)-2-oxoazepan-3-ylcarbamate (4.79 g, 14.1 mmol) in toluene (250 mL) and the mixture was heated to 90° C. After 1 h, the reaction was allowed to cool to ambient temperature and concentrated. Purification by silica gel chromatography (100% dichloromethane→85% dichloromethane/ethyl acetate) gave a white solid. This solid was repurified by silica gel chromatography (20% ethyl acetate/ hexanes→30% ethyl acetate/hexanes) to give the title compound (4.81 g). MS 357.0 (M+1). $^1$H NMR (500 MHz, CDCl$_3$) δ 8.30 (s, 1H), 7.10-7.04 (m, 2H), 6.94-6.91 (m, 1H), 6.50 (d, J=6.1 Hz, 1H), 4.62 (dd, J=10.3, 3.7 Hz, 1H), 4.13-3.88 (m, 1H), 3.36 (dd, J=14.7, 7.1 Hz, 1H), 3.07 (t, J=11.2 Hz, 1H), 2.32-2.21 (m, 2H), 2.14-2.12 (m, 1H), 1.79-1.72 (m, 1H), 1.47 (s, 9H).

Alternatively, tert-Butyl (3R,6S)-6-(2,3-difluorophenyl)-2-oxoazepan-3-ylcarbamate (Step F of Intermediate 4 preparation) can be made in the following manner:

Step H. 1-Benzyl 5-methyl N,N-bis(tert-butoxycarbonyl)-D-glutamate

To a solution of Boc-D-Glu-OBn (50.0 g, 148.2 mmol) in DCM (400 ml) and MeOH (100 ml) was added trimethylsilyldiazomethane (88.9 mL of 2.0 M solution in hexanes, 117.8 mmol) at 0° C. dropwise via an addition funnel. After 60 min the reaction was concentrated. This residue was diluted with CH$_3$CN (400 mL) and (Boc)$_2$O (48.5 g, 222.3 mmol) was added followed by DMAP (18.1 g, 14.8 mmol). After 24 h the reaction was concentrated and purified by silica gel chromatography (10%→60% ethyl acetate/hexanes) to give the title compound (48.20 g, 72%). MS 252.2 (M+1−2Boc).

Step I. Benzyl (2R,5E)-2-[bis(tert-butoxycarbonyl) amino]-6-nitrohex-5-enoate To a −78° C. of 1-benzyl 5-methyl N,N-bis(tert-butoxycarbonyl)-D-glutamate (48.2 g, 106.8 mmol) in Et$_2$O (400 mL), was added DIBAL (133.4 mL of 1.0 M solution in toluene, 133.4 mmol) slowly so as not to let the internal temperature exceed −65° C. After 15 min, 20 mL more of DIBAL was added. After stirring for additional 20 min, water (300 mL) was added and the reaction was warmed to room temperature and stirred for 30 min. This mixture was further diluted with Et$_2$O and H$_2$O, the layers separated and the aqueous phase extracted with more Et$_2$O. The combined organics extracts were washed with a saturated aqueous solution of sodium potassium tartrate (2×), brine, dried over magnesium sulfate, filtered and concentrated to give benzyl N,N-bis(tert-butoxycarbonyl)-5-oxo-D-norvalinate (44.4 g) which was carried directly into the next step. MS 444.1 (M+Na). This material was dissolved in toluene (310 mL) and nitromethane (57.1 mL, 1.05 mol) and 1,1,3,3-tetramethylguanidine (1.3 mL, 10.5 mmol) were added at 0° C. After stirring for 30 min the nitroaldol reaction was complete, so methanesulfonyl chloride (12.2 mL, 158 mmol) was added followed triethylamine (22.0 mL, 158 mmol) at 0° C. and the reaction was allowed to warm to RT. After 1 h, 4 mL MsCl and 5.5 mL triethylamine were added. After stirring for an additional 30 min the mixture was diluted with Et$_2$O and NaHCO$_3$, the phases separated and the aqueous layer backwashed with another portion of Et$_2$O. The combined organics were dried over magnesium sulfate, filtered and concentrated to give a residue that was purified by silica gel chromatography (5%→50% ethyl acetate/hexanes) to give the title compound (34.3 g, 70%). MS 487.1 (M+Na).

Step J. Benzyl (5S)-N,N-bis(tert-butoxycarbonyl)-5-(2,3-difluorophenyl)-6-nitro-D-norleucinate A solution of benzyl (2R,5E)-2-[bis(tert-butoxycarbonyl) amino]-6-nitrohex-5-enoate (34.0 g, 73.2 mmol), 2,3-difluorophenylboronic acid (28.9 g, 183.0 mmol) and water (4.62 mL, 256.2 mmol) in dioxane (240 mL) was degassed with argon for 15 min. To this solution was added sodium bicarbonate (3.08 g, 36.6 mmol), (S)-BINAP (1.28 g, 2.05 mmol) and acetylacetanotobis(ethylene)rhodium(I) (0.472 g, 1.83 mmol). The mixture was stirred at RT for 2 min then heated to 35° C. After 4 h, 255 mg of (S)-BINAP and 94 mg of acetylacetanotobis(ethylene)rhodium(I) were added. After an additional 2 h the reaction was diluted with DCM/NaHCO$_3$, the layers separated and the aqueous phase was backwashed with another portion of DCM. The combined organics were dried over magnesium sulfate, filtered and concentrated to give a residue that was purified by silica gel chromatography (5%→60% ethyl acetate/hexanes) to give the title compound (37.0 g, 87%) contaminated with ~5% 5R isomer. MS 379.1 (M+1−Boc).

Step K. (5S)-N$^2$,N$^2$-Bis(tert-butoxycarbonyl)-5-(2,3-difluorophenyl)-D-lysine A solution of benzyl (5S)-N,N-bis(tert-butoxycarbonyl)-5-(2,3-difluorophenyl)-6-nitro-D-norleucinate (15.5 g, 26.8 mmol) and 10% Pd/C (12.0 g) in EtOH (175 mL, SureSeal from Aldrich), was hydrogenated at 55 psi overnight. After 18 h, another 4 g of 10% Pd/C was added and the reaction hydrogenated at 55 psi for another 18 h. The reaction was filtered through Celite with more EtOH and concentrated to afford the title compound (12.0 g). MS 459.2 (M+1).

Step L. tert-Butyl (3R,6S)-6-(2,3-difluorophenyl)-2-oxoazepan-3-ylcarbamate

To a solution (5S)-N$^2$,N$^2$-bis(tert-butoxycarbonyl)-5-(2,3-difluorophenyl)-D-lysine (22.0 g, 48.0 mmol) in DCM (700 mL) were added EDC (11.0 g, 57.6 mmol) and HOAT (3.27 g, 24.0 mmol) followed by triethylamine (10.0 mL, 72.0 mmol). After 60 min, NaHCO$_3$ was added, the layers separated and the aqueous phase backwashed with DCM. The combined organics were dried over magnesium sulfate, filtered and concentrated. The residue was purified by silica gel chromatography (10% MeOH/DCM) to give the cyclized compound (18.0 g). A portion of this material (2.60 g, 5.90 mmol) was diluted DCM (60 mL) and TFA (1.20 mL, 11.8 mmol) was added. After 1 h, NaHCO$_3$ was added, the layers separated and the aqueous phase backwashed with DCM. The combined organics were dried over magnesium sulfate, filtered and concentrated and the residue purified by silica gel chromatography (5%→50% EtOAc/DCM) to give the title compound (1.14 g). MS 341.1 (M+1).

Intermediate 5

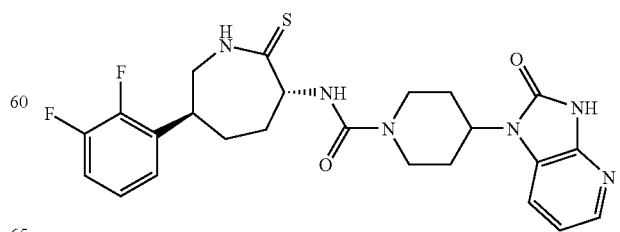

N-[(3R,6S)-6-(2,3-Difluorophenyl)-2-thioxoazepan-3-yl]-4-(2-oxo-2,3-dihydro-1H-imidazo[4,5-b]pyridin-1-yl)piperidine-1-carboxamide Step A: (3R,6S)-3-Amino-6-(2,3-difluorophenyl)azepane-2-thione Trifluoroacetic acid (5 mL, 49.6 mmol) was added to a solution of tert-butyl (3R,6S)-6-(2,3-difluorophenyl)-2-thioxoazepan-3-ylcarbamate (680 mg, 1.91 mmol) in dichloromethane (10 mL). After 1 h, the reaction was concentrated. Saturated aqueous sodium bicarbonate was added and the mixture was extracted with dichloromethane (3×). The combined organic extracts were dried over magnesium sulfate, filtered, and concentrated to give the title compound (489 g). MS 257.0 (M+1).

Step B: N-[(3R,6S)-6-(2,3-Difluorophenyl)-2-thioxoazepan-3-yl]-4-(2-oxo-2,3-dihydro-1H-imidazo[4,5-b]pyridin-1-yl)piperidine-1-carboxamide Triethylamine (0.45 mL, 3.25 mmol) was added to a solution of tert-butyl (3R,6S)-6-(2,3-difluorophenyl)-2-thioxoazepan-3-ylcarbamate (416 mg, 1.62 mmol) and 4-(2-oxo-2,3-dihydro-1H-imidazo[4,5-b]pyridin-1-yl)piperidine-1-carbonyl chloride (466 mg, 1.66 mmol) in dichloromethane (70 mL) and the mixture heated to reflux. After 18 h, the mixture was allowed to cool to ambient temperature and concentrated. Purification by silica gel chromatography (100% dichloromethane o 95% dichloromethane/methanol) gave the title compound (685 mg). MS 501.0 (M+1).

Intermediate 6

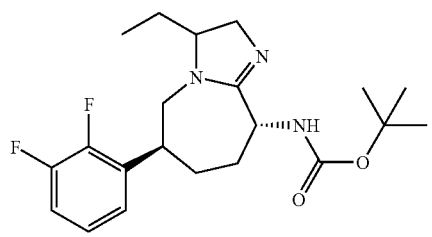

tert-Butyl [(6S,9R)-6-(2,3-difluorophenyl)-3-2,5,6,7,8,9-hexahydro-3H-imidazo[1,2-a]azepin-9-yl]carbamate Step A: tert-Butyl {(3R,6S)-6-(2,3-difluorophenyl)-2-[(2-hydroxybutyl)imino]azepan-3-yl}carbamate Mercury(II) chloride (174 mg, 0.640 mmol) was added to a solution of tert-butyl [(3R,6S)-6-(2,3-difluorophenyl)-2-thioxoazepan-3-yl]carbamate (190 mg, 0.533 mmol) and 1-aminobutan-2-ol (152 µL, 1.60 mmol) in ethanol (5 mL) at 55° C. After 30 min, the reaction was allowed to cool to ambient temperature. The mixture was filtered and concentrated. Saturated aqueous sodium carbonate was added and the mixture was extracted with dichloromethane (3×). The combined organic extracts were dried over sodium sulfate, filtered, and concentrated to give the title compound (238 mg). MS 412.2 (M+1).

Step B: tert-Butyl [(6S,9R)-6-(2,3-difluorophenyl-3-ethyl-2,5,6,7,8,9-hexahydro-3H-imidazo[1,2-a]azepin-9-yl]carbamate Methanesulfonyl chloride (204 µL, 1.79 mmol) was added to a solution of tert-butyl {(3R,6S)-6-(2,3-difluorophenyl)-2-[(2-hydroxybutyl)imino]azepan-3-yl}carbamate (223 mg, 0.542 mmol) and triethylamine (378 µL, 2.71 mmol) in acetonitrile (15 mL) at 0° C. The mixture was allowed to warm to ambient temperature. After 18 h, saturated aqueous sodium bicarbonate was added and the mixture was extracted with dichloromethane (2×). The combined organic extracts were dried over magnesium sulfate, filtered, and concentrated. Purification by silica gel chromatography [100% dichloromethane→90% dichloromethane/(10% ammonium hydroxide/methanol)] gave the title compound (122 mg). MS 394.2 (M+1).

Intermediate 7

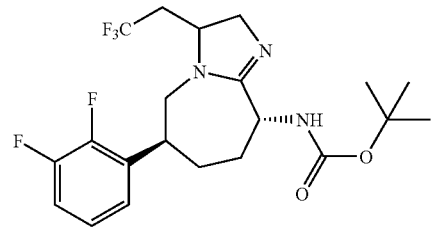

tert-Butyl [(6S,9R)-6-(2,3-difluorophenyl)-3-(2,2,2-trifluoroethyl)-2,5,6,7,8,9-hex hydro-3H-imidazo[1,2-a]azepin-9-yl]carbamate Prepared essentially following the procedure outlined for the preparation of Intermediate 6. MS 448.2 (M+1).

Example 1

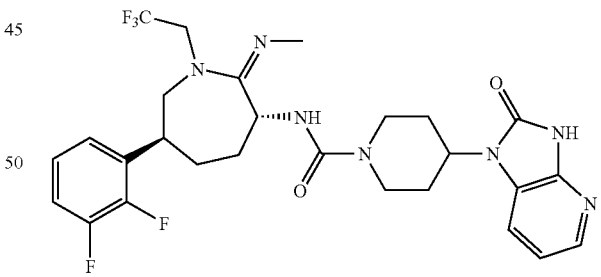

N-[(3R,6S)-6-(2,3-Difluorophenyl)-2-(methylimino)-1-(2,2,2-trifluoroethyl)azepan-3-yl]-4-(2-oxo-2,3-dihydro-1H-imidazo[4,5-b]pyridin-1-yl)piperidine-1-carboxamide Step A: tert-Butyl [(3R,6S)-6-(2,3-difluorophenyl)-2-thioxo-1-(2,2,2-trifluoroethyl)azepan-3-yl]carbamate Sodium hydride (60% dispersion in mineral oil; 39 mg, 0.975 mmol) was added to a solution of tert-butyl [(3R,6S)-

6-(2,3-difluorophenyl)-2-thioxoazepan-3-yl]carbamate (202 mg, 0.567 mmol) and 2,2,2-trifluoroethyl trifluoromethanesulfonate (141 μL, 1.131 mmol) in N,N-dimethylformamide at −25° C. After 15 min, water was added, and the mixture was extracted with ethyl acetate. The organic layer was washed with water (2×), brine, dried over sodium sulfate, filtered and concentrated. Purification by silica gel chromatography (0% hexanes→30% ethyl acetate/hexanes) gave the title compound (105 mg). MS 439.1 (M+1).

Step B: (3R,6S)-3-Amino-6-(2,3-difluorophenyl)-1-(2,2,2-trifluoroethyl)azepane-2-thione Hydrochloric acid (4.0 M in dioxane; 3 mL, 12.0 mmol) was added to a solution of tert-butyl [(3R,6S)-6-(2,3-difluorophenyl)-2-thioxo-1-(2,2,2-trifluoroethyl)azepan-3-yl]carbamate (105 mg, 0.239 mmol) in 1,4-dioxane (3 mL). After 1 h, the reaction was concentrated to give the title compound as a bis hydrochloride salt (96 mg). MS 339.1 (M+1).

Step C: N-[(3R,6S)-6-(2,3-Difluorophenyl)-2-thioxo-1-(2,2,2-trifluoroethyl)azepan-3-yl]-4-(2-oxo-2,3-dihydro-1H-imidazo[4,5-b]pyridin-1-yl)piperidine-1-carboxamide Triethylamine (100 μL, 0.720 mmol) was added to a solution of the bis hydrochloride salt of (3R,6S)-3-amino-6-(2,3-difluorophenyl)-1-(2,2,2-trifluoroethyl)azepane-2-thione (90 mg, 0.240 mmol) and 4-(2-oxo-2,3-dihydro-1H-imidazo[4,5-b]pyridin-1-yl)piperidine-1-carbonyl chloride (74 mg, 0.264 mmol) in dichloromethane (10 mL) and the mixture heated to reflux. After 18 h, the reaction was allowed to cool to ambient temperature, water was added and the mixture was extracted with dichloromethane (3×). The combined organic extracts were dried over sodium sulfate, filtered, and concentrated. Purification by silica gel chromatography (100% dichloromethane→95% dichloromethane/methanol) gave the title compound (78 mg). MS 583.2 (M+1).

Step D: N-[(3R,6S)-6-(2,3-Difluorophenyl)-2-(methylimino)-1-(2,2,2-trifluoroethyl)azepan-3-yl]-4-(2-oxo-2,3-dihydro-1H-imidazo[4,5-b]pyridin-1-yl)piperidine-1-carboxamide Mercury(II) chloride (23 mg, 0.084 mmol) was added to a solution of N-[(3R,6S)-6-(2,3-difluorophenyl)-2-thioxo-1-(2,2,2-trifluoroethyl)azepan-3-yl]-4-(2-oxo-2,3-dihydro-1H-imidazo[4,5-b]pyridin-1-yl)piperidine-1-carboxamide (32 mg, 0.055 mmol) and methylamine (2.0 M in tetrahydrofuran; 274 μL, 0.547 mmol) in ethanol (1 mL). After 2 h, the mixture was filtered and concentrated. Purification by reverse phase HPLC(C-18, 95% water/acetonitrile→100% acetonitrile with 0.1% trifluoroacetic acid) gave the title compound as a bis trifluoroacetate salt (33 mg). MS 580.2415 (M+1).

Essentially following the procedure outlined for the preparation of Example 1, the Examples in Table 1 were prepared.

TABLE 1

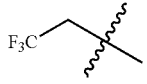

| Example | R¹ | R² | MS (M + 1) |
|---|---|---|---|
| 2 | H | H | 484.2252 |
| 3 | H | CH₃ | 498.2444 |
| 4 | H | 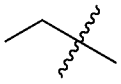 | 566.2333 |
| 5 | 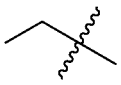 | H | 512.2538 |
| 6 | 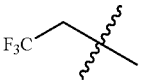 | CH₃ | 526.2741 |
| 7 | 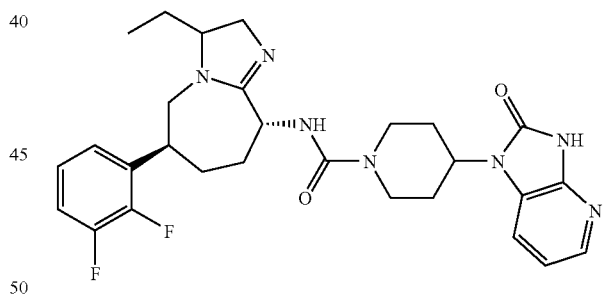 | H | 566.2270 |

Example 8

N-[(6S,9R)-6-(2,3-Difluorophenyl)-3-ethyl-2,5,6,7,8,9-hexahydro-3H-imidazo[1,2-a]azepin-9-yl]-4-(2-oxo-2,3-dihydro-1H-imidazo[4,5-b]pyridin-1-yl)piperidine-1-carboxamide Step A: (6S,9R)-6-(2,3-Difluorophenyl)-3-ethyl-2,5,6,7,8,9-hexahydro-3H-imidazo[1,2-a]azepin-9-amine Hydrochloric acid (4.0 M in dioxane; 3 mL, 12.0 mmol) was added to a solution of tert-butyl [(6S,9R)-6-(2,3-difluorophenyl)-3-ethyl-2,5,6,7,8,9-hexahydro-3H-imidazo[1,2-a]azepin-9-yl]carbamate (122 mg, 0.310 mmol) in 1,4-dioxane (3 mL). After 1 h, the reaction was concentrated to give the title compound as a bis hydrochloride salt (136 mg). MS 294.1 (M+1).

Step B: N-[(6S,9R)-6-(2,3-Difluorophenyl)-3-ethyl-2,5,6,7,8,9-hexahydro-3H-imidazo[1,2-a]azepin-9-yl]-4-(2-oxo-2,3-dihydro-1H-imidazo[4,5-b]pyridin-1-yl)piperidine-1-carboxamide Triethylamine (17 µL, 0.124 mmol) was added to a solution of the (6S,9R)-6-(2,3-difluorophenyl)-3-ethyl-2,5,6,7,8,9-hexahydro-3H-imidazo[1,2-a]azepin-9-amine (13 mg, 0.035 mmol) and 4-(2-oxo-2,3-dihydro-1H-imidazo[4,5-b]pyridin-1-yl)piperidine-1-carbonyl chloride (15 mg, 0.053 mmol) in dichloromethane (1 mL). After 18 h, saturated aqueous sodium bicarbonate was added and the mixture was extracted with dichloromethane (3×). The combined organic extracts were dried over sodium sulfate, filtered, and concentrated. Purification by reverse phase HPLC(C-18, 95% water/acetonitrile 30% water/acetonitrile with 0.1% trifluoroacetic acid) gave the title compound (8 mg). MS 538.2710 (M+1).

Example 9

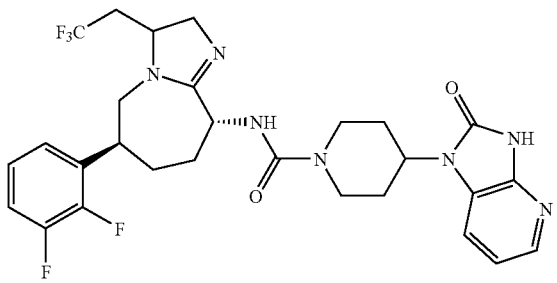

N-[(6R,9R)-6-(2,3-Difluorophenyl)-3-(2,2,2-trifluoroethyl)-2,5,6,7,8,9-hexahydro-3H-imidazo[1,2-a]azepin-9-yl]-4-(2-oxo-2,3-dihydro-1H-imidazo[4,5-b]pyridin-1-yl)piperidine-1-carboxamide Prepared essentially following the procedure outlined for the preparation of Example 8. MS 592.2408 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of Formula I:

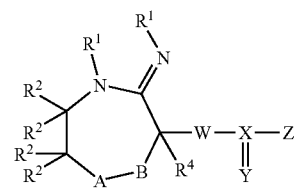

wherein:
Z is selected from:

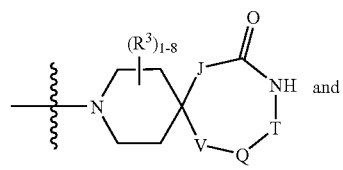

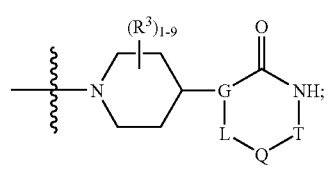

A is $C(R^2)_2$;
B is $(C(R^2)_2)_n$;
$R^1$ is independently selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_pC_{1-3}$ alkyl,
   g) halogen,
   h) $OR^4$,
   i) $O(CH_2)_sOR^4$,
   j) $CO_2R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2NR^{10}R^{11}$,
   q) $N(R^{10})SO_2R^{11}$,
   r) $S(O)_mR^{10}$,
   s) CN,
   t) $NR^{10}R^{11}$,
   u) $N(R^{10})(CO)NR^4R^{11}$, and,
   v) $O(CO)R^4$;
2) aryl or heteroaryl, unsubstituted or substituted with one or more substituents each independently selected from:

a) $C_{1-6}$ alkyl,
b) $C_{3-6}$ cycloalkyl,
c) aryl, unsubstituted or substituted with 1-5 substituents each independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_p C_{1-3}$ alkyl,
g) halogen,
h) $OR^4$,
i) $O(CH_2)_s OR^4$,
j) $CO_2 R^4$,
k) $(CO)NR^{10}R^{11}$,
l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2 NR^{10}R^{11}$,
q) $N(R^{10})SO_2 R^{11}$,
r) $S(O)_m R^{10}$,
s) CN,
t) $NR^{10}R^{11}$,
u) $N(R^{10})(CO)NR^4 R^{11}$, and
v) $O(CO)R^4$;
where any two independent $R^1$ and the atom or atoms to which they are attached optionally join to form a ring selected from $C_{5-7}$ heterocycle, including dihydro-imidazolyl, tetrahydro-pyrimidyl, and tetrahydro-diazepinyl;

$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents each independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents each independently selected from $R^4$,
  e) heterocycle, unsubstituted or substituted with 1-5 substituents each independently selected from $R^4$,
  $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and,
  v) $O(CO)R^4$;
2) aryl or heteroaryl, unsubstituted or substituted with one or more substituents each independently selected from:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents each independently selected from $R^4$,
  e) heterocycle, unsubstituted or substituted with 1-5 substituents each independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$,
  l) $O(CO)NR^{10}R^{11}$,
  m) $N(R^4)(CO)NR^{10}R^{11}$,
  n) $N(R^{10})(CO)R^{11}$,
  o) $N(R^{10})(CO)OR^{11}$,
  p) $SO_2 NR^{10}R^{11}$,
  q) $N(R^{10})SO_2 R^{11}$,
  r) $S(O)_m R^{10}$,
  s) CN,
  t) $NR^{10}R^{11}$,
  u) $N(R^{10})(CO)NR^4 R^{11}$, and
  v) $O(CO)R^4$,
where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl, and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl, or morpholinyl, which is ring is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;
X is C or S;
Y is O, $(R^4)_2$, NCN, $NSO_2 CH_3$ or $NCONH_2$, or Y is $O_2$ when X is S;

$R^6$ is independently selected from H and:
  a) $C_{1-6}$ alkyl,
  b) $C_{3-6}$ cycloalkyl,
  c) aryl, unsubstituted or substituted with 1-5 substituents where the substituents are independently selected from $R^4$,
  d) heteroaryl, unsubstituted or substituted with 1-5 substituents each independently selected from $R^4$,
  e) heterocycle, unsubstituted or substituted with 1-5 substituents each independently selected from $R^4$,
  f) $(F)_p C_{1-3}$ alkyl,
  g) halogen,
  h) $OR^4$,
  i) $O(CH_2)_s OR^4$,
  j) $CO_2 R^4$,
  k) $(CO)NR^{10}R^{11}$, l) $O(CO)NR^{10}R^{11}$,
m) $N(R^4)(CO)NR^{10}R^{11}$,
n) $N(R^{10})(CO)R^{11}$,
o) $N(R^{10})(CO)OR^{11}$,
p) $SO_2NR^{10}R^{11}$,
q) $N(R^{10})SO_2R^{11}$,
r) $S(O)_mR^{10}$,
s) CN,
t) $NR^{10}R^{11}$,
u) $N(R^{10})(CO)NR^4R^{11}$, and
v) $O(CO)R^4$;

J is a bond, $C(R^6)_2$, O or $NR^6$;

V is selected from a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$, and $N(R^6)$—$N(R^6)$;

G-L is selected from: N,N—$C(R^6)_2$, C=$C(R^6)$, C=N, $C(R^6)$, $C(R^6)$—$C(R^6)_2$, $C(R^6)$—$C(R^6)_2$—$C(R^6)_2$, C=$C(R^6)$—$C(R^6)_2$, $C(R^6)$—$C(R^6)$=$C(R^6)$, $C(R^6)$—$C(R^6)_2$—$N(R^6)$, C=$C(R^6)$—$N(R^6)$, $C(R^6)$—$C(R^6)$=N, $C(R^6)$—$N(R^6)$—$C(R^6)_2$, C=N—$C(R^6)_2$, $C(R^6)$—N=$C(R^6)$, $C(R^6)$—$N(R^6)$—$N(R^6)$, C=N—$N(R^6)$, N—$C(R^6)_2$—$C(R^6)_2$, N—$C(R^6)$=$C(R^6)$, N—$C(R^6)_2$—$N(R^6)$, N—$C(R^6)$=N, N—$N(R^6)$—$C(R^6)_2$ and N—N=$C(R^6)$;

Q is independently selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;

T is independently selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$ cycloalkyl, aryl, heterocycle, and heteroaryl, which ring is unsubstituted or substituted with 1-10 substituents each independently selected from $R^6$;

p is 0 to 2q+1, for a substituent with q carbons;
m is 0, 1 or 2;
n is 1;
s is 1, 2 or 3;

"heteroaryl" is a 5- to 7-membered monocyclic- or 9- to 10-membered fused bicyclic heterocyclic ring system which contains an aromatic ring, any ring of which may be saturated partially saturated, or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring;

"heterocyclic" is a 5- to 7-membered monocyclic- or 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may be optionally be quaternized, and including any bicyclic group in which any of the above-defined heterocyclic rings is fused to a benzene ring;

or a pharmaceutically acceptable salt and individual diastereomers thereof.

2. A compound of claim 1 having the formula Ia:

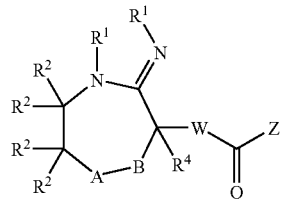

wherein:
A is a bond, $C(R^2)_2$, O, $S(O)_m$ or $NR^2$;
B is $(C(R^2)_2)_n$;
n is 0 or 1; and
or a pharmaceutically acceptable salt and individual stereoisomers thereof.

3. The compound of claim 1, wherein:
$R^1$ is selected from:
1) H, $C_1$-$C_6$ alkyl, $C_{3-6}$ cycloalkyl and heterocycle, unsubstituted or substituted with one or more substituents each independently selected from:
a) $C_{1-6}$ alkyl,
b) $C_{3-6}$ cycloalkyl,
c) aryl, unsubstituted or substituted with 1-5 substituents where the substituents are independently selected from $R^4$,
d) heteroaryl, unsubstituted or substituted with 1-5 substituents each independently selected from $R^4$,
e) heterocycle, unsubstituted or substituted with 1-5 substituents each independently selected from $R^4$,
f) $(F)_pC_{1-3}$ alkyl,
g) halogen,
h) $OR^4$,
i) $O(CH_2)_sOR^4$,
j) $CO_2R^4$,
k) CN,
l) $NR^{10}R^{11}$, and
m) $O(CO)R^4$; and
2) aryl or heteroaryl, unsubstituted or substituted with one or more substituents independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and,
m) $O(CO)R^4$;
where any two independent $R^1$ and the atom or atoms to which they are attached optionally join to form a ring selected from $C_{5-7}$ heterocycle, including dihydro-imidazolyl, tetrahydro-pyrimidyl, and tetrahydro-diazepinyl;

$R^2$ is selected from:
1) H, $C_0$-$C_6$ alkyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents where the substituents are independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and
2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$,
   where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

$R^6$ is independently selected from H and:
a) $C_{1-6}$ alkyl,
b) $C_{3-6}$ cycloalkyl,
c) $(F)_p C_{1-3}$ alkyl,
d) halogen,
e) $OR^4$,
f) $CO_2 R^4$,
g) $(CO)NR^{10}R^{11}$,
h) $SO_2 NR^{10}R^{11}$,
i) $N(R^{10})SO_2 R^{11}$,
j) $S(O)_m R^4$,
k) CN,
l) $NR^{10}R^{11}$ and
m) $O(CO)R^4$; and Z is Z1 and:
J is a bond and V is a bond, or
J is a bond, V is a bond and T is —C(=O)—, or
J is a bond, V is a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$ or $N(R^6)$—$N(R^6)$, or
J is a bond, $C(R^5)_2$, O, or $NR^5$, V is a bond,
or Z is Z2 and G-L is selected from N, N—$C(R^6)_2$, C=C $(R^6)$, C=N and N—$C(R^6)_2$—$C(R^6)_2$;

Q is independently selected from:
(1) =$C(R^{7a})$—,
(2) —$C(R^{7a})_2$—,
(3) —C(=O)—,
(4) —$S(O)_m$—,
(5) =N—, and
(6) —$N(R^{7a})$—;

T is independently selected from:
(1) =$C(R^{7b})$—,
(2) —$C(R^{7b})_2$—,
(3) —C(=O)—,
(4) —$S(O)_m$—,
(5) =N—, and
(6) —$N(R^{7b})$—;

$R^3$ is independently selected from H, substituted or unsubstituted $C_1$-$C_3$ alkyl, F, CN and $CO_2 R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl, which ring is unsubstituted or substituted with 1-10 substituents each independently selected from $R^6$;

p is 0 to 2q+1, for a substituent with q carbons
m is 0 to 2;
s is 1 to 3;
or a pharmaceutically acceptable salt and individual stereoisomers thereof.

4. The compound of claim 1, wherein:
$R^1$ is selected from:
1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$, and where heteroaryl is selected from:
      imidazole, isoxazole, oxazole, pyrazine, pyrazole, pyridazine, pyridine, pyrimidine, and thiazole;
   e) heterocycle, unsubstituted or substituted with 1-5 substituents each independently selected from $R^4$, and where heterocycle is selected from: azetidine, dioxane, dioxolane, morpholine, oxetane, piperazine, piperidine, pyrrolidine, tetrahydrofuran, and tetrahydropyran;

f) $(F)_pC_{1-3}$ alkyl,
g) halogen,
h) $OR^4$,
i) $O(CH_2)_sOR^4$,
j) $CO_2R^4$,
k) CN,
l) $NR^{10}R^{11}$,
m) $O(CO)R^4$;

2) aryl or heteroaryl, selected from: phenyl, imidazole, isoxazole, oxazole, pyrazine, pyrazole, pyridazine, pyridine, pyrimidine, and thiazole,
unsubstituted or substituted with one or more substituents each independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$;

$R^2$ is selected from:
1) H, $C_0$-$C_6$ alkyl, $C_{3-6}$ cycloalkyl and heterocycle, unsubstituted or substituted with one or more substituents each independently selected from:
a) $C_{1-6}$ alkyl,
b) $C_{3-6}$ cycloalkyl,
c) phenyl, unsubstituted or substituted with 1-5 substituents each independently selected from $R^4$,
d) heteroaryl, unsubstituted or substituted with 1-5 substituents each independently selected from $R^4$, and where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
e) heterocycle, unsubstituted or substituted with 1-5 substituents where the substituents are independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
f) $(F)_pC_{1-3}$ alkyl,
g) halogen,
h) $OR^4$,
i) $O(CH_2)_nOR^4$,
j) $CO_2R^4$,
k) CN,
l) $NR^{10}R^{11}$, and
m) $O(CO)R^4$; and 2) aryl or heteroaryl, selected from:
phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, unsubstituted or substituted with one or more substituents each independently selected from:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$, where any two independent $R^2$ on the same or adjacent atoms optionally join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, $R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and phenyl, unsubstituted or substituted with hydroxy or $C_1$-$C_6$ alkoxy;

W is NO or $C(R^4)_2$;

$R^6$ is independently selected from H and:
a) $C_{1-6}$ alkyl,
b) $C_{3-6}$ cycloalkyl,
c) $(F)_pC_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_mR^4$,
k) CN,
l) $NR^{10}R^{11}$, and
m) $O(CO)R^4$;

Z is Z1 and:
J is a bond, V is a bond, Q is —$N(R^{7a})$—, and T is —C(=O)—, or
J is a bond, V is a bond, Q is —$C(R^{7a})_2$—, and T is —C(=O)—, or
J is a bond, V is a bond, Q is N=, and T is =$C(R^{7b})$—, or
J is a bond, V is a bond, Q is —$C(R^{7a})_2$—, and T is —$C(R^{7b})_2$—, or
J is a bond, V is a bond, Q is $C(R^{7a})$=, T is =$C(R^{7b})$—, where the atoms to which $R^{7a}$ and $R^{7b}$ are attached join to form a benzene, pyridine, or diazine ring, or
J is a bond, V is $C(R^6)_2$, Q is —$C(R^{7a})$=, T is =$C(R^{7b})$—, and the atoms to which $R^{7a}$ and $R^{7b}$ are attached join to form a benzene, or pyridine ring, or
J is O, V is a bond, Q is —$C(R^{7a})$=, T is =$C(R^{7b})$—, and the atoms to which $R^{7a}$ and $R^{7b}$ are attached are joined together to form a benzene, or pyridine ring, or Z is Z2 and:

G-L is N, Q is —C($R^{7a}$)$_2$—, and T is —C($R^{7b}$)$_2$—, or
G-L is N, Q is —C($R^{7a}$)= and T is =C($R^{7b}$)—, or
G-L is N, Q is N=, and T is =C($R^{7b}$)—, or
G-L is N, Q is —C($R^{7a}$)$_2$—, and T is —C(O)—, or
G-L is C=C($R^6$), Q is —C($R^{7a}$)= and T is =C($R^{7b}$)—, or
G-L is C=C($R^6$), Q is —C($R^{7a}$)= and T is =N—, or
G-L is C=C($R^6$), Q is —N= and T is =C($R^{7b}$)—, or
G-L is C=N, Q is —C($R^{7a}$)= and T is =C($R^{7b}$)—, or
G-L is N, Q is —C($R^{7a}$)=, and T is =C($R^{7b}$)—, and the atoms to which $R^{7a}$ and $R^{7b}$ are attached join to form a benzene, pyridine, or diazine ring, or
G-L is N—C($R^6$)$_2$, Q is —C($R^{7a}$)=, and T is =C($R^{7b}$)—, and the atoms to which $R^{7a}$ and $R^{7b}$ are attached join to form a benzene, or pyridine ring, or
G-J is C=N, Q is —C($R^{7a}$)=, and T is =C($R^{7b}$)—, and the atoms to which $R^{7a}$ and $R^{7b}$ are attached are join to form a benzene ring, or
G-L is C=C($R^6$), Q is C($R^{7a}$)=, and T is =C($R^{7b}$)—, and the atoms to which $R^{7a}$ and $R^{7b}$ are attached join to form a benzene ring, or
G-L is N—C($R^6$)$_2$—C($R^6$)$_2$, Q is —C($R^{7a}$)=, and T is =C($R^{7b}$)—, and the atoms to which $R^{7a}$ and $R^{7b}$ are attached join to form a benzene ring;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom or atoms to which they are attached optionally join to form a ring selected from $C_{3-6}$cycloalkyl, aryl, heterocycle, and heteroaryl which is unsubstituted or substituted with 1-10 substituents each independently selected from $R^6$;

p is 0 to 2q+1, for a substituent with q carbons m is 0 to 2;

s is 1 to 3;

or a pharmaceutically acceptable salt and individual stereoisomers thereof.

5. A compound selected from:

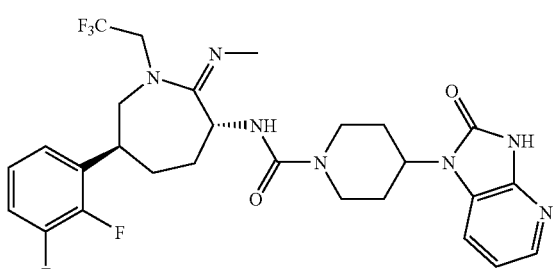

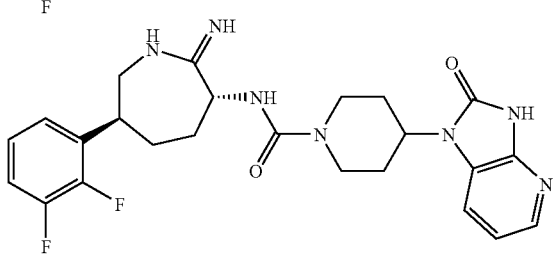

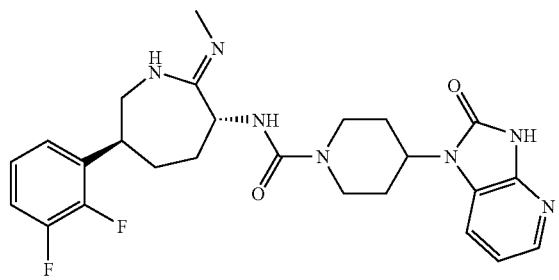

-continued

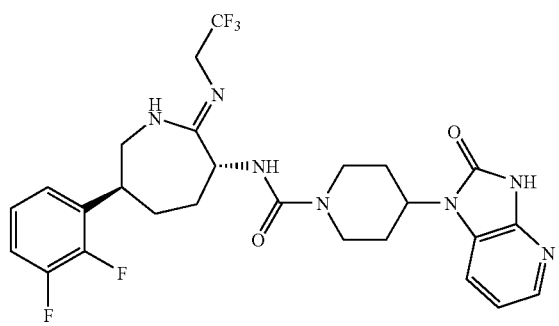

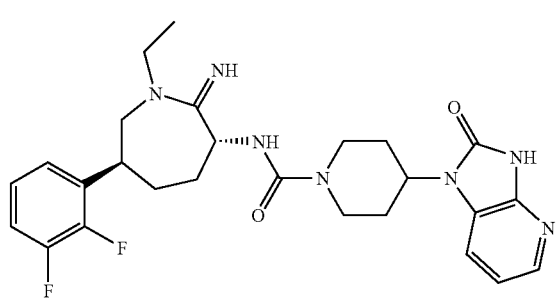

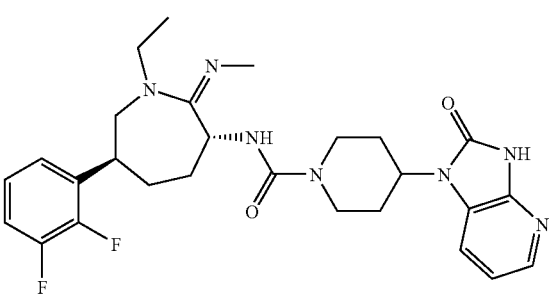

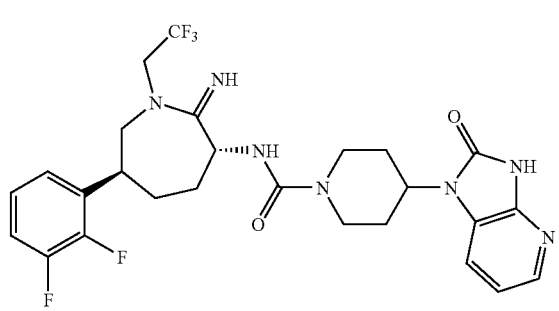

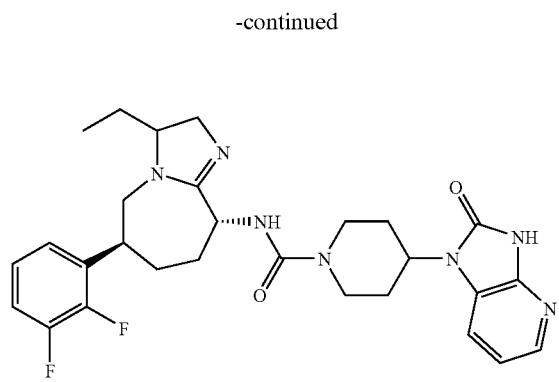
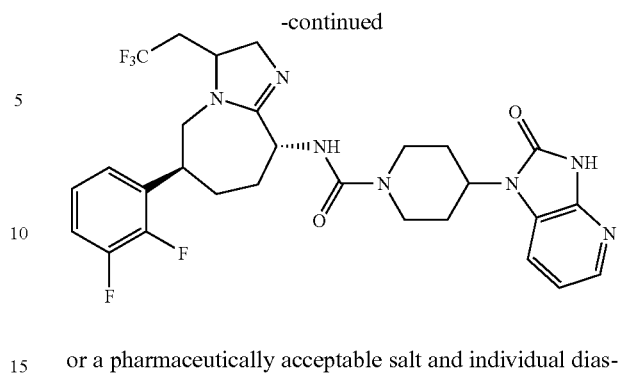
or a pharmaceutically acceptable salt and individual diastereomers thereof.
6. A pharmaceutical composition which comprises an inert carrier and the compound of claim 1.
* * * * *